United States Patent
Chaudhri et al.

(10) Patent No.: US 11,903,730 B1
(45) Date of Patent: Feb. 20, 2024

(54) BODY FAT MEASUREMENTS FROM A TWO-DIMENSIONAL IMAGE

(71) Applicant: Amazon Technologies, Inc., Seattle, WA (US)

(72) Inventors: Apoorv Chaudhri, Cupertino, CA (US); Siddhartha Chandra, Santa Clara, CA (US); Prakash Ramu, Portland, OR (US); Amit Kumar Agrawal, Santa Clara, CA (US); Sigal Raab, Sde Warburg (IL); Anantharanga Prithviraj, Santa Clara, CA (US); Ram Sever, Sunnyvale, CA (US); Ita Lifshitz, Kiryat Ono (IL); Ayush Sharma, Seattle, WA (US); Anna Shtengel, Santa Clara, CA (US); Gal Levi, Givataim (IL); Rajesh Gautam, Cupertino, CA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 16/582,840

(22) Filed: Sep. 25, 2019

(51) Int. Cl.
*A61B 5/00* (2006.01)
*G06T 7/11* (2017.01)
(Continued)

(52) U.S. Cl.
CPC .......... *A61B 5/4872* (2013.01); *A61B 5/0077* (2013.01); *A61B 5/7264* (2013.01);
(Continued)

(58) Field of Classification Search
CPC ... A61B 5/4872; A61B 5/0077; A61B 5/7264; A61B 5/7278; A61B 5/742;
(Continued)

(56) References Cited

U.S. PATENT DOCUMENTS 6,188,925 B1 * 2/2001 Kawanishi ........... A61B 5/4869
600/547
6,468,209 B1 * 10/2002 Heymsfield .......... A61B 5/0537
128/897

(Continued)

FOREIGN PATENT DOCUMENTS

CA        2884668 A1    9/2016
CN      106295205 A *   1/2017
(Continued)

OTHER PUBLICATIONS

Pradhan et al., Feature Extraction from 2D Images for Body Composition Analysis, 2015 IEEE 978-1-5090-0379-2/15, DOI 10.1109/ISM.2015.117, pp. 45-52. (Year: 2015).*

(Continued)

*Primary Examiner* — Ishrat I Sherali
(74) *Attorney, Agent, or Firm* — Athorus, PLLC

(57) ABSTRACT

Described are systems and methods that use one or more two-dimensional ("2D") body images of a body to determine body fat measurements of that body. For example, a standard 2D camera of a portable device, such as a cell phone, tablet, laptop, etc., may be used to generate one or more 2D body images of a user. Those 2D body images, or image, may be processed using the disclosed implementations to determine a body fat measurement of the body represented in the image.

22 Claims, 15 Drawing Sheets

(51) Int. Cl.
*G06T 7/194* (2017.01)
*G06T 3/40* (2006.01)
*G06T 7/00* (2017.01)
*G06N 3/04* (2006.01)
*G06N 3/08* (2006.01)
*G16H 30/40* (2018.01)
*G06T 7/60* (2017.01)

(52) U.S. Cl.
CPC ............ *A61B 5/7278* (2013.01); *A61B 5/742* (2013.01); *G06N 3/04* (2013.01); *G06N 3/08* (2013.01); *G06T 3/40* (2013.01); *G06T 7/0014* (2013.01); *G06T 7/11* (2017.01); *G06T 7/194* (2017.01); *G06T 7/60* (2013.01); *G16H 30/40* (2018.01); *A61B 2560/0431* (2013.01); *A61B 2576/00* (2013.01); *G06T 2207/20084* (2013.01); *G06T 2207/30196* (2013.01)

(58) Field of Classification Search
CPC ........ A61B 2560/0431; A61B 2560/00; G06T 7/194; G06T 7/11; G06T 3/40; G06T 7/0014; G06T 7/60; G06T 2207/20084; G06T 2207/30196; G16H 30/40; G06N 3/04; G06N 3/08
See application file for complete search history.

(56) References Cited

U.S. PATENT DOCUMENTS

| | | | |
|---|---|---|---|
| 8,918,162 | B2 | 12/2014 | Prokoski |
| 8,982,147 | B2 | 3/2015 | Ramani et al. |
| 9,801,550 | B2 * | 10/2017 | Ferrantelli .............. A61B 5/107 |
| 9,839,376 | B1 * | 12/2017 | Ross ...................... A61B 5/742 |
| 10,321,728 | B1 * | 6/2019 | Koh ..................... G06K 9/00369 |
| 10,489,683 | B1 | 11/2019 | Koh et al. |
| 10,559,111 | B2 | 2/2020 | Sachs et al. |
| 10,636,158 | B1 | 4/2020 | Kamiyama et al. |
| 10,748,217 | B1 * | 8/2020 | Ross ...................... G06Q 50/22 |
| 10,926,404 | B2 | 2/2021 | Jackson et al. |
| 10,945,813 | B2 | 3/2021 | Li et al. |
| 11,069,131 | B2 * | 7/2021 | Agrawal ................ G16H 15/00 |
| 11,232,629 | B1 * | 1/2022 | Seymore ................ H04N 23/63 |
| 11,423,630 | B1 * | 8/2022 | Agrawal .................... G06T 7/55 |
| 2004/0151366 | A1 | 8/2004 | Nefian et al. |
| 2005/0251347 | A1 | 11/2005 | Perona et al. |
| 2006/0061583 | A1 | 3/2006 | Spooner et al. |
| 2006/0222206 | A1 | 10/2006 | Garoutte |
| 2013/0325493 | A1 | 12/2013 | Wong et al. |
| 2014/0121564 | A1 * | 5/2014 | Raskin .................. A61B 5/0022 600/587 |
| 2014/0340479 | A1 | 11/2014 | Moore et al. |
| 2015/0154453 | A1 | 6/2015 | Wilf |
| 2016/0247017 | A1 | 8/2016 | Sareen et al. |
| 2016/0284123 | A1 | 9/2016 | Hare et al. |
| 2017/0273639 | A1 * | 9/2017 | Iscoe ...................... G06N 20/00 |
| 2018/0089821 | A1 | 3/2018 | Koldyshev |
| 2018/0289334 | A1 | 10/2018 | Brouwer et al. |
| 2019/0122424 | A1 | 4/2019 | Moore et al. |
| 2019/0191137 | A1 | 6/2019 | Bisti |
| 2019/0347817 | A1 * | 11/2019 | Ferrantelli ........... G06K 9/6256 |
| 2020/0193710 | A1 | 6/2020 | Talgorn et al. |
| 2020/0319015 | A1 * | 10/2020 | Kamiyama .......... A61B 5/1075 |
| 2021/0097759 | A1 | 4/2021 | Agrawal et al. |
| 2021/0232924 | A1 | 7/2021 | Sun et al. |
| 2022/0147735 | A1 | 5/2022 | Suh et al. |
| 2022/0292351 | A1 | 9/2022 | Etemad et al. |
| 2023/0065288 | A1 | 3/2023 | Valsan et al. |

FOREIGN PATENT DOCUMENTS

| | | | |
|---|---|---|---|
| CN | 108652584 | A * | 10/2018 |
| CN | 110051353 | A * | 7/2019 |
| WO | 2022204343 | A1 | 9/2022 |

OTHER PUBLICATIONS

Anguelov, D., Srinivasan, P., Koller, D., Thrun, S., Rodgers, J. and Davis, J., "SCAPE: Shape Completion and Animation of People," ACM Trans. Graph. (Proc. SIGGRAPH), 24(3):408-416, Jul. 2005, 9 pages, http://robots.stanford.edu/papers/anguelov.shapecomp.pdf.

Balan, A. O. and Black, M. J., "The Naked Truth: Estimating Body Shape under Clothing," In European Conference on Computer Vision (ECCV), 2008, 15 pages, https://www.researchgate.net/profile/Michael_Black6/publication/221305001_The_Naked_Truth_Estimating_Body_Shape_Under_Clothing/links/0fcfd512d21f538458000000/The-Naked-Truth-Estimating-Body-Shape-Under-Clothing.pdf?origin=publication_detail.

Bălan, A. O., Sigal, L., Black, M. J., Davis, J. E. and Haussecker, H. W., "Detailed Human Shape and Pose from Images," In IEEE Conference on Computer Vision and Pattern Recognition (CVPR), 2007, 9 pages.

Bogo, F., Kanazawa, A., Lassner, C., Gehler, P., Romero, J. and Black, M. J., "Keep it SMPL: Automatic Estimation of 3D Human Pose and Shape from a Single Image," In European Conference on Computer Vision (ECCV), 2016, 21 pages, https://arxiv.org/pdf/1607.08128v1.pdf.

Boisvert, J., Shu, C., Wuhrer, S., and Xi, P., "Three-Dimensional Human Shape Inference from Silhouettes: Reconstruction and Validation," Machine Vision and Applications, 24(1):145-157, 2013, 13 pages, http://people.scs.carleton.ca/~c_shu/Publications/silhouettes_human_rec_MVA11.pdf.

Chen, X., Guo, Y., Zhou, B. and Zhao, Q., "Deformable Model for Estimating Clothing and Naked Human Shapes from a Single Image," The Visual Computer, 29(11):1187-1196, 2013, 10 pages.

Chen, Y., Kim, T.-K. and Cipolla, R., "Inferring 3D Shapes and Deformations from Single Views," In European Conference on Computer Vision, 2010, 14 pages.

Chen, Y., Kim, T.-K. and Cipolla, R., Silhouette-Based Object Phenotype Recognition Using 3D Shape Priors. In Inter-national Conference on Computer Vision (ICCV), 2011, 8 pages.

Devries, T. and Taylor, G. W., Learning Confidence for Out-of-Distribution Detection in Neural Networks, arXiv preprint arXiv:1802.04865, 2018, 12 pages.

Dibra, E., Jain, H., Öztireli, C., Ziegler, R. and Gross, M., "HSNets: Estimating Human Body Shape from Silhouettes with Convolutional Neural Networks," In International Conference on 3D Vision (3DV), 2016, 10 pages.

Dibra, E., Jain, H., Öztireli, C., Ziegler, R. and Gross, M., "Human Shape from Silhouettes Using Generative HKS Descriptors and Cross-Modal Neural Networks," In IEEE Conference on Computer Vision and Pattern Recognition (CVPR), 2017, 11 pages.

Dibra, E., Jain, H., Öztireli, C., Ziegler, R. and Gross, M., "Shape from Selfies: Human Body Shape Estimation Using CCA Regression Forests," In European Converence on Computer Vision (ECCV), 2016, 17 pages.

Gilbert, A., Volino, M., Collomosse, J. and Hilton, A.,"Volumetric Performance Capture from Minimal Camera View-Points," In European Conference on Computer Vision, 2018, 16 pages.

Gong, K., Liang, X., Zhang, D., Shen, X. and Lin, L., "Look into Person: Self-Supervised Structure-Sensitive Learning and a New Benchmark for Human Parsing," In IEEE Conference on Computer Vision and Pattern Recognition (CVPR), 2017, 9 pages.

Guan, P., Weiss, A., Bălan, A. O. and Black, M. J., "Estimating Human Shape and Pose from a Single Image," In IEEE International Conference on Computer Vision (ICCV), 2009, 8 pages.

Güler, R. A., Neverova, N. and Kokkinos, I., "DensePose: Dense Human Pose Estimation in the Wild," In IEEE Conference on Computer Vision and Pattern Recognition (CVPR), 2018, 10 pages.

He, K., Zhang, X., Ren, S. and Sun, J., "Deep Residual Learning for Image Recognition," In IEEE Conference on Computer Vision and Pattern Recognition (CVPR), 2016, 9 pages.

Horprasert, T., Harwood, D. and Davis, L. S., "A Statistical Approach for Real-Time Robust Background Subtraction and Shadow Detection," In IEEE International Conference on Computer Vision (ICCV), 1999, 19 pages.

(56) References Cited

OTHER PUBLICATIONS

Joo, H., Simon, T. and Y. Sheikh, Y., "Total Capture: A 3D Deformation Model for Tracking Faces, Hands, and Bodies," In IEEE Conference on Computer Vision and Pattern Recognition (CVPR), 2018, 10 pages.
Kanazawa, A., Black, M. J., Jacobs, D. W. and Malik, J., "End-to-End Recovery of Human Shape and Pose," In IEEE Conference on Computer Vision and Pattern Recognition (CVPR), 2018, 10 pages.
Krasin, I., Duerig, T., Alldrin, N., Ferrari, V., Abu-El-Haija, S., Kuznetsova, A., Rom, H., Uijlings, J., Popov, S., Kamali, S., Malloci, M., Pont-Tuset, J., Veit, A., Belongie, S., Gomes, V., Gupta, A., Sun, C., Chechik, G., Cai, D., Feng, Z., Narayanan, D., and Murphy, K., "Openimages: A Public Dataset for Large-Scale Multi-Label and Multi-Class Image Classification," Dataset available from https://storage.googleapis.com/openimages/web/index.html, 2017.
Kundu, A., Li, Y. and Rehg, J. M., "3D-RCNN: Instance-Level 3D Object Reconstruction via Render-and-Compare," In IEEE Conference on Computer Vision and Pattern Recognition (CVPR), 2018, 10 pages.
Lassner, C., Romero, J., Kiefel, M., Bogo, F., Black, M. J. and Gehler, P. V., "Unite the People—Closing the Loop Between 3D and 2D Human Representations," In IEEE Conference on Computer Vision and Pattern Recognition (CVPR), 2017, 10 pages.
Long, J., Shelhamer, E., and Darrell, T., "Fully Convolutional Networks for Semantic Segmentation,"In IEEE Conference on Computer Vision and Pattern Recognition (CVPR), 2015, 10 pages.
Loper, M., Mahmood, N., Romero, J., Pons-Moll, G. and Black, M. J., "SMPL: A Skinned Multi-Person Linear Model," ACM Trans. Graphics (Proc. SIGGRAPH Asia), 34(6):248:1-248:16, Oct. 2015, 16 pages.
Ngiam, J., Khosla, A., Kim, M., Nam, J., Lee, H.and Ng, A. Y., "Multimodal Deep Learning," In International Conference on Machine Learning (ICML), pp. 689-696, 2011, 8 pages.
Omran, M., Lassner, C., Pons-Moll, G., Gehler, P. V. and Schiele, B., "Neural Body Fitting: Unifying Deep Learning and Model-Based Human Pose and Shape Estimation," In International Conference on 3D Vision (3DV), 2018, 13 pages.
Pavlakos, G., Zhu, L., Zhou, X. and Daniilidis, K., "Learning to Estimate 3D Human Pose and Shape from a Single Color Image," In IEEE Conference on Computer Vision and Pattern Recognition (CVPR), 2018, 10 pages.
Popa, A.-I., Zanfir, M. and C. Sminchisescu, C., "Deep Multitask Architecture for Integrated 2D and 3D Human Sensing," In IEEE Conference on Computer Vision and Pattern Recognition (CVPR), 2017, 10 pages.
Rhodin, H., Robertini, N., Casas, D., Richardt, C., Seidel, H.-P. and Theobalt, C., "General Automatic Human Shape and Motion Capture Using Volumetric Contour Cues," In European Conference on Computer Vision, 2016, 18 pages.
Robinette, K. M., Blackwell, S., Daanen, H., Boehmer, M., Fleming, S., Brill, T., Hoeferlin, D. and Burnsides, D., "Civilian American and European Surface Anthropometry Resource (CAESAR) Final Report," Tech. Rep. AFRL-HEWP-TR-2002-0169, US Air Force Research Laboratory, 2002, 70 pages.
Sigal, L., Bălan, A. O. and Black, M. J., "Combined Discriminative and Generative Articulated Pose and Non-Rigid Shape Estimation," In Neural Information Processing Systems (NIPS), 2007, 8 pages.
Sun, J., Ovsjanikov, M. and Guibas, L., "A Concise and Provably Informative Multi-Scale Signature Based on Heat Diffusion," In Symposium on Geometry Processing, 2009, 10 pages.
Tan, J. K. V., Budvytis, I. and Cipolla, R., "Indirect Deep Structured Learning for 3D Human Body Shape and Pose Prediction," In British Machine Vision Conference, 2017, 11 pages.
TC2 Labs LLC, "SizeUSA", 3 pages, http://scan2fit.com/sizeusa/about.php.
Varol, G., Ceylan, D., Russell, B., Yang, J., Yumer, E., Laptev, I. and Schmid, C., "BodyNet: Volumetric Inference of 3D Human Body Shapes," In European Conference on Computer Vision (ECCV), 2018, 17 pages.
Varol, G., Romero, J., Martin, X., Mahmood, N., Black, M. J., Laptev, I. and Schmid, C., "Learning from Synthetic Humans," In IEEE Conference on Computer Vision and Pattern Recognition (CVPR), 2017, 9 pages.
Xi, P., Lee, W.-S. and Shu, C., "A Data-Driven Approach to Human-Body Cloning Using a Segmented Body Database," In Pacific Conference on Computer Graphics and Applications (PG), 2007, 9 pages.
Yu, F., Zhang, Y., Song, S., Seff, A., and Xiao, J., "LSUN: Construction of a Large-Scale Image Dataset Using Deep Learning with Humans in the Loop," arXiv preprint arXiv:1506.03365, 2015, 9 pages.
Zanfir, A., Marinoiu, E. and Sminchisescu, C., "Monocular 3D Pose and Shape Estimation of Multiple People in Natural Scenes—the Importance of Multiple Scene Constraints," In IEEE Conference on Computer Vision and Pattern Recognition (CVPR), 2018, 10 pages.
Zhang, H., Dana, K., Shi, J., Zhang, Z., Wang, X., Tyagi, A. and Agrawal, A., "Context Encoding for Semantic Segmentation," In the IEEE Conference on Computer Vision and Pattern Recognition (CVPR), Jun. 2018, 10 pages.
Bukar et al., "Automatic age and gender classification using supervised appearance model," Journal of Electronic Imaging, Aug. 2016; 25(6):0601605, 12 pages.
Nguyen et al., "Gender Recognition from Human-Body Images Using Visible-Light and Thermal Camera Videos Based on a Convolutional Neural Network for Image Feature Extraction," Sensors,Mar. 2017:17(3);637, 22 pages.
Pavlakos et al., "Expressive Body Capture: 3D Hands, Face, and Body from a Single Image," 2019 IEEE/CVF Conference on Computer Vision and Pattern Recognition (CVPR), Jun. 1, 2019, 11 pages.
Su et al., "Multi-view Convolutional Neural Networks for 3D Shape Recognition," 2015 IEEE International Conference on Computer Vision (ICCV), Dec. 7-13, 2015, Santiago, Chile, 9 pages.
Chen, W., Wang, H., Li, Y., Su, H., Wang, Z., Tu, C., Lischinski, D., Cohen-Or, D. and Chen, B. Synthesizing Training Images for Boosting Human 3D Pose Estimation. In 2016 Fourth International Conference on 3D Vision (3DV) Oct. 25, 2016 (pp. 479-488). IEEE, 10 pages.
Hirano, D., Funayama, Y. and Maekawa, T. 3D Shape Reconstruction From 2D Images. Computer-Aided Design and Applications. 2009 CAD Solutions, LLC. Jan. 1, 2009 ;6(5):701-10, 10 pages.
Mülayim, A. Y., Yilmaz, U. and Atalay, V. Silhouette-based 3D Model Reconstruction from Multiple Images. IEEE Transactions on Systems, Man, and Cybernetics, Part B (Cybernetics). Jul. 22, 2003;33(4):582-91, 27 pages.
Park, S., Hwang, J. and Kwak, N. 3D Human Pose Estimation Using Convolutional Neural Networks with 2D Pose Information. In European Conference on Computer Vision, Sep. 8, 2016 (pp. 156-169), https://arxiv.org/pdf/1608.03075v2.pdf, 15 pages.
Rogez, G., Weinzaepfel, P. and Schmid C. LCR-Net++: Multi-Person 2D and 3D Pose Detection in Natural Images. IEEE IEEE Transactions on Pattern Analysis and Machine Intelligence, Jan. 14, 2019;42(5): 1146-61, Downloaded on Jul. 18, 2020, 16 pages.
Sun, X., Wu, J., Zhang, X., Zhang, Z., Zhang, C., Xue, T., Tenenbaum, J. B. and Freeman, W. T. Pix3D: Dataset and Methods for Single-Image 3D Shape Modeling. In 2018 IEEE/CVF Conference on Computer Vision and Pattern Recognition, Jun. 18, 2018 (pp. 2974-2983). IEEE, 10 pages.
Tome, D., Russell, C. and Agapito, L. Lifting from the Deep: Convolutional 3D Pose Estimation from a Single Image. In Proceedings of the IEEE Conference on Computer Vision and Pattern Recognition 2017 (pp. 2500-2509), 11 pages.
Xie, H., Yao, H., Sun, X., Zhou, S. and Zhang, S. Pix2Vox: Context-aware 3D Reconstruction from Single and Multi-view Images. arXiv preprint arXiv: 1901.11153, https://arxiv.org/pdf/1901.11153.pdf, Jul. 29, 2019, 9 pages.
Anonymous: "BMI 3D", www.bmi3d.de; Nov. 25, 2018 (Nov. 25, 2018), XP002801424,URL: https://web.archive.org/web/20181125231845/https://www.bmi3d.de/rechner.html [Retrieved from the Internet on Dec. 16, 2020]; the whole document.
Anonymous: "Documentation: What is MakeHuman?", MakeHuman, May 20, 2016 (May 20, 2016), XP002801426, URL: http://

(56) References Cited

OTHER PUBLICATIONS www.makehumancommunity.org/wiki/Documentation:What is MakeHuman%3F [Retrieved from the Internet on Jan. 30, 2021]; the whole document.

Anonymous: "Virtual Weight Loss Simulator", www.changeinseconds. com; Dec. 11, 2016 (Dec. 11, 2016), XP002801425, URL: https://web.archive.org/web/20161206202928;%20/http://www.changeinseconds.com/simulator/ [Retrieved from the Internet on Dec. 16, 2020]; the whole document.

nakedlabs.com, Aug. 2, 2018 (Aug. 2, 2018), XP002801423, URL: https://web.archive.org/web/20180802014000/https://nakedlabs.com/ [Retrieved from the Internet: Dec. 16, 2020]; the whole document.

Hassan B, Izquierdo E and Piatrik T. Soft Biometrics: A Survey Benchmark Analysis, Open Challenges and Recommendations. Multimedia Tools and Applications. Mar. 2, 2021, 44 pages.

Nambiar A, Bernardino A and Nascimento J. Shape Context for Soft Biometrics in Person Re-Identification and Database Retrieval. Pattern Recognition Letters. Dec. 15, 2015; 68:297-305.

Ramanathan V and Wechsler H. Robust Human Authentication Using Appearance and Holistic Anthropometric Features. Pattern Recognition Letters. Nov. 1, 2010; 31(15):2425-35.

Varol G, Ceylan D, Russell B, Yang J, Yumer E, Laptev I and Schmid C. Bodynet: Volumetric Inference of 3D Human Body Shapes (and Supplemental Material). In Proceedings of the European Conference on Computer Vision (ECCV) 2018 (pp. 20-36).

Zhao, Ruiqi, Yan Wang, and Aleix M. Martinez. "A Simple, Fast and Highly-Accurate Algorithm to Recover 3D Shape from 2D Landmarks on a Single Image." IEEE Transactions on Pattern Analysis and Machine Intelligence, vol. 40, No. 12 (2017): 3059-3066. (Year: 2018).

Kolotouros, N. et al. "Learning to Reconstruct 3D Human Pose and Shape via Model-fitting in the Loop," In Proceedings of the IEEE International Conference on Computer Vision, 2019, Sep. 27, 2019, URL: https://arxiv.org/abs/1909.12828, 10 pages.

Sengupta, A. et al. "Hierarchical Kinematic Probability Distributions for 3D Human Shape and Pose Estimation from Images in the Wild," In International Conference on Computer Vision, Oct. 2021, URL: https://www.researchgate.net/publication/355060401_Hierarchical_Kinematic_Probability_Distributions_for_3D_Human_Shape_and_Pose_Estimation_from_Images_in_the_Wild, 17 pages.

Sengupta, A. et al. "Synthetic Training for Accurate 3D Human Pose and Shape Estimation in the Wild," In British Machine Vision Conference (BMVC), Sep. 2020, URL: https://www.researchgate.net/publication/344335326_Synthetic_Training_for_Accurate_3D_Human_Pose_and_Shape_Estimation_in_the_Wild, 13 pages.

Dibra Endri et al: "HS-Nets: Estimating Human Body Shape from Silhouettes with Convolutional Neural Networks", 2016 Fourth International Conference On 30 Vision (30V), IEEE, Oct. 25, 2016 (Oct. 25, 2016), pp. 108-117, XP033027616, DOI: 10.1109/3DV.2016.19 [retrieved on Dec. 15, 2016].

Grinciunaite, A., et al., "Human Pose Estimation in Space and Time Using 3D CNN," ECCV Workshop on Brave New Ideas for Motion Representations in Videos, Oct. 19, 2016, URL: https://arxiv.org/pdf/1609.00036.pdf, 7 pages.

Li, K., R. Garg, M. Cai and I. Reid, "Single-view Object Shape Reconstruction Using Deep Shape Prior and Silhouette," The School of Computer Science, University of Adelaide and Australian Centre for Robotic Vision. Adelaide, Australia, arXiv preprint arXiv: 1811.11921. Aug. 1, 2019, Cornell University, URL: https://arxiv.org/pdf/1811.11921.pdf, 14 pages.

Wiles, Olivia and Andrew Zisserman, "SilNet: Single- and Multi-View Reconstruction by Learning from Silhouettes," Visual Geometry Group, Department of Engineering Science, University of Oxford, Oxford, UK, arXiv preprint arXiv: 1711.07888. Nov. 21, 2017, Cornell University, URL: https://arxiv.org/pdf/1711.07888.pdf, 13 pages.

Zhu, R., H. Kiani Galoogahi, C. Wang and S. Lucey, "Rethinking Reprojection: Closing the Loop for Pose-aware Shape Reconstruction from a Single Image," The Robotics Institute, Carnegie Mellon University, In Proceedings of the IEEE International Conference on Computer Vision, Jul. 26, 2017 (pp. 57-65), 9 pages.

Dibra, Endri: "Recovery of the 3D Virtual Human: Monocular Estimation of 3D Shape and Pose with Data Driven Priors", May 31, 2018 (May 31, 2018), pp. 1-192, XP055648769, DOI: 10.3929/ethz-b-000266852 Retrieved from the Internet: URL: https://www.research-collection.ethz.ch/bitstream/handle/20.500.11850/266852/Endri_Dibra_Thesis_Final.pdf?sequence=3&isAllowed=y [retrieved on Dec. 3, 2019].

Huang Z, Barrett JS, Barrett K, Barrett R, Ng CM. Novel method to predict body weight in children based on age and morphological facial features. The Journal of Clinical Pharmacology. Apr. 2015;55(4):447-51.

Ji, Z., et al.; "Human Body Shape Reconstruction from Binary Silhouette Images;" Computer Aided Geometric Design 71 (2019) pp. 231-243; Elsevier B.V. (Year: 2019).

Kocabey E, Camurcu M, Ofli F, Aytar Y, Marin J, Torralba A, Weber I. Face-to-BMI: Using computer vision to infer body mass index on social media. In Proceedings of the International AAAI Conference on Web and Social Media May 3, 2017 (vol. 11, No. 1, pp. 572-575).

Lee BJ, Jang JS, Kim JY. Prediction of body mass index from facial features of females and males. International Journal of Bio-Science and Bio-Technology. Sep. 2012;4(3):45-62.

Lee BJ, Kim JY. Predicting visceral obesity based on facial characteristics. BMC Complementary and Alternative Medicine. Dec. 2014; 14(1):1-9.

Smith, Brandon M. et al: "Towards Accurate 3D Human Body Reconstruction from Silhouettes", 2019 International Conference On 3D Vision (3DV), IEEE, Sep. 16, 2019 (Sep. 16, 2019), pp. 279-288, XP033653362, DOI: 10.1109/3DV.2019.00039 [retrieved on Oct. 28, 2019].

Yan, Song et al: "Learning Anthropometry from Rendered Humans", arxiv.org, Cornell University Library, 201 Online Library Cornell University Ithaca, NY, 14853, Jan. 7, 2021 (Jan. 7, 2021), XP081853690.

Kato H, Ushiku Y, Harada T. Neural 3D Mesh Renderer. In Proceedings of the IEEE Conference on Computer Vision and Pattern Recognition 2018 (pp. 3907-3916).

Natsume R, Saito S, Huang Z, Chen W, Ma C, Li H, Morishima S. SiCloPe: Silhouette-Based Clothed People. arXiv preprint arXiv: 1901.00049. Dec. 31, 2018.

Biggs, Benjamin, et al. "3D Multi-bodies: Fitting Sets of Plausible 3D Human Models to Ambiguous Image Data." Advances in Neural Information Processing Systems 34 (2020): 20496-20507. (Year: 2020).

Seo, Hyewon, Young In Yeo, and Kwangyun Wahn. "3D Body Reconstruction from Photos Based on Range Scan." International Conference on Technologies for E-Learning and Digital Entertainment. Springer-Verlag, Berlin, Heidelberg, 2006. pp. 849-860 (Year: 2006).

Zhang, Tianshu, Buzhen Huang, and Yangang Wang. "Object-Occluded Human Shape and Pose Estimation from a Single Color Image." Proceedings of the I EEE/CVF Conference on Computer Vision and Pattern Recognition. 2020. (Year: 2020) 10 pages.

* cited by examiner

BODY FAT MEASUREMENTS FROM A TWO-DIMENSIONAL IMAGE

BACKGROUND

Existing body fat measurement techniques are either low cost and highly inaccurate, or require large and expensive equipment, along with trained staff, to obtain more accurate results. For example, body calipers and bioelectrical impedance, often found on bathroom scales, are relatively low cost solutions for determining body fat of a body. However, in general, both are highly inaccurate. At the other end of the spectrum are Air Displacement Plethysmograph (ADP) systems that use whole body densitometry to determine body composition (fat vs. lean). Another example includes Dual-energy X-ray absorptiometry (DXA or DEXA) systems that use low-dose X-rays to determine body composition, including body fat. While ADP and DEXA systems are considered highly accurate, they require expensive equipment and trained staff to operate and, in the case of DEXA, may have some negative health related effects due to the use of X-rays.

DETAILED DESCRIPTION

As is set forth in greater detail below, implementations of the present disclosure are directed to the use of one or more two-dimensional ("2D") body images of a body to determine body fat measurements of that body. For example, a standard 2D camera of a portable device, such as a cell phone, tablet, laptop, etc., may be used to generate one or more 2D body images of a user. Those 2D body images, or image, may be processed using the disclosed implementations to determine a body fat measurement of the body represented in the image.

In some implementations, a single image that includes a representation that is less than all of the body may be used to determine body fat measurements of that body. For example, if the image only includes the torso of the body, that portion may be used to determine an overall bodyfat measurement for the body. In other examples, a head of the body, a leg of the body, an arm of the body, alone or in combination may be used with the disclosed implementations to determine body fat measurements for the body. In still other examples, other inputs may be used in conjunction with the 2D body image to determine body fat measurements for the body. Other inputs include, but are not limited to, age, height, weight, gender, ethnicity, etc., each of which may be used with the 2D body image to determine body fat measurements for the body represented in the 2D body image. As will be discussed in further detail below, the 2D body images may be obtained as part of a user providing images to an application for use in determining body fat measurements. In other implementations, the 2D body images may be any image generated by an imaging element of the device and/or any other 2D image that includes all or a portion of a body of a user.

In some implementations, the body fat measurements may be presented to a user by an application executing on a portable device that provides other information about the body. For example, as discussed further below, the 2D body images may also be used to generate a 3D body model of the body of the user, and/or other body composition information (e.g., weight, visual body fat, bone mass, body mass, body volume, etc.) and body dimensions (e.g., arm length, leg length, arm circumference, leg circumference, shoulder width, shoulder circumference, waist width, waist circumference, torso width, torso circumference, body height, etc.). The application executing on the portable device may present the 3D body model, the body fat measurements, and some or all of the body composition information and/or body dimensions. The user may interact with the application to view different sides of the 3D body model and/or to visualize differences in the 3D body model if one or more body measurements change.

Figure 1:
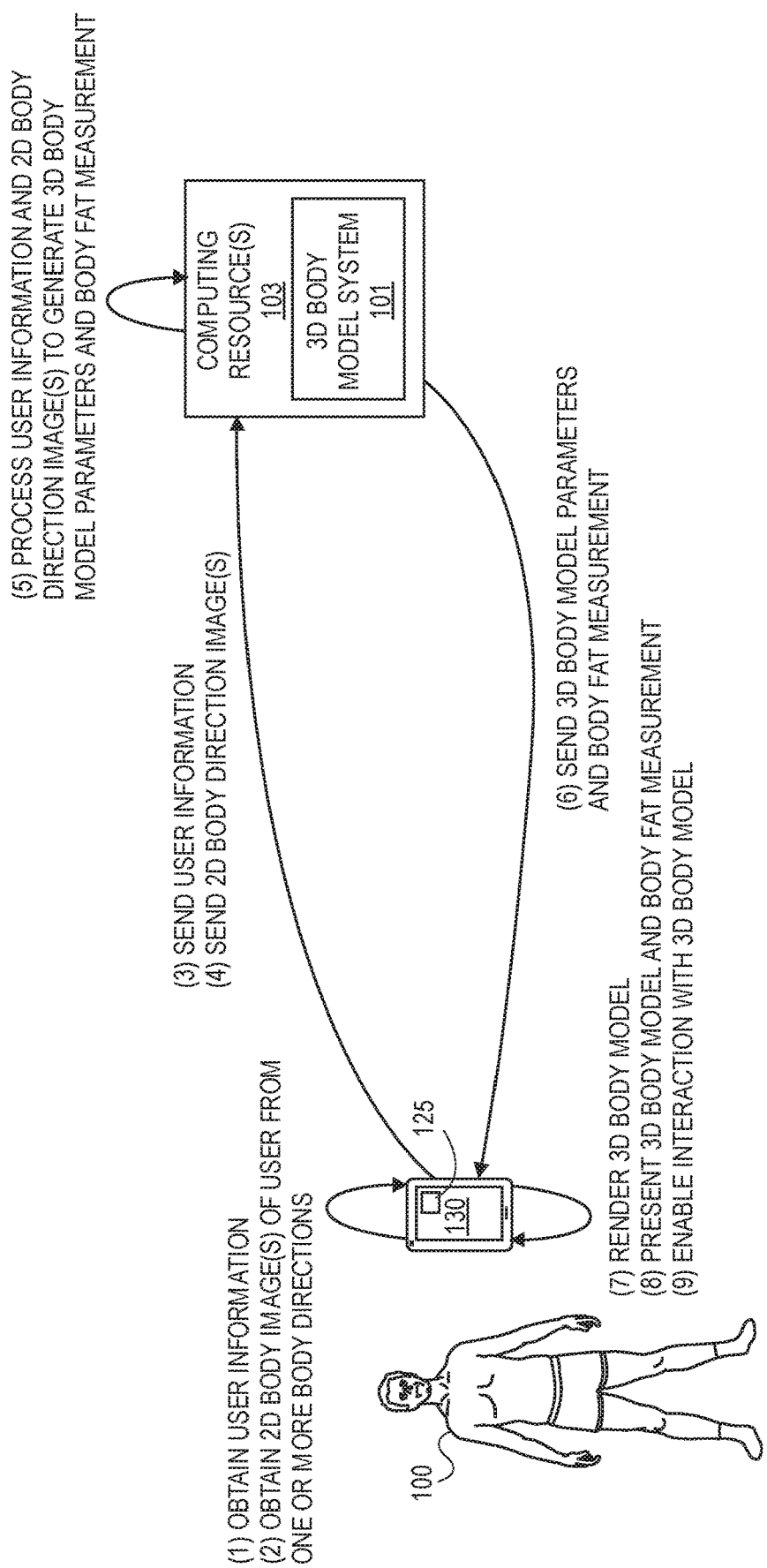
FIG. 1 is a transition diagram of two-dimensional body image collection and processing to produce a dimensionally accurate three-dimensional body model and body fat measurements of that body that are presented back to the user, in accordance with implementations of the present disclosure.

FIG. 1 is a transition diagram of 2D body image collection and processing to produce a dimensionally accurate 3D body model and body fat measurement of a body of a user 100 that is presented back to the user, in accordance with implementations of the present disclosure.

In some implementations, a user 100 may execute an application 125 on a portable device 130, such as a cellular phone, tablet, laptop, etc., that includes an imaging element (e.g., camera) and interact with the application. The imaging element may be any conventional imaging element, such as a standard 2D Red, Green, Blue ("RGB") digital camera that is included on many current portable devices. Likewise, images, as discussed herein may be still images generated by the imaging element and/or images or frames extracted from video generated by the imaging element.

The user may provide user information, such as username, password, etc., to the application so that the application can identify the user and determine a user account associated with the user. Likewise, the user may provide other user information, such as body measurements, including but not limited to weight, height, age, gender, ethnicity, etc. The user may select which user information is provided or choose not to provide any user information. In addition, in some implementations, the user may interact with the application executing on the portable device 130 without providing any user identifying information (e.g., operate as a guest to the application).

Upon user identification and/or receipt of user information, the user 100 positions the portable device 130 such that a field of view of the imaging element of the portable device is substantially horizontal and facing toward the user. In some implementations, the application 125 executing on the portable device 130 may provide visual and/or audible instructions that guide the user 100 in the placement and positioning of the portable device 130. For example, the application may instruct the user 100 to place the portable device 130 between waist and head height of the user and in a substantially vertical direction (e.g., between 2 and 10 degrees of vertical) such that the imaging element is pointed toward the user and the field of view of the imaging element is substantially horizontal.

In some implementations, the application may request that the user wear a minimal amount of clothing, such as undergarments shown in FIG. 1. By wearing minimal clothing, processing of the 2D body image may be more accurate.

Once the portable device is properly positioned, 2D body images of the user 100 are captured by the imaging element of the portable device 130. As discussed in more detail below, those 2D body images are processed to determine that the user is in a defined pose, such as an "A Pose," and to determine a body direction of the body of the user with respect to the camera. The defined pose may be any body position that enables image capture of components of the body. In one example, the defined pose is an "A Pose" in which the arms are separated from the sides of the body and the legs are separated, for example by separating the feet of the body to about shoulder width. The A Pose allows image processing of 2D body images to distinguish between body parts (e.g., legs, arms, torso) from different angles and also aids in body direction determination. The body direction may be any direction or orientation of the body with respect to the imaging element. Example body directions include, but are not limited to, a front side body direction in which the body is facing the imaging element, a right side body direction in which the body is turned such that a right side of the body is facing the imaging element, a left side body direction in which a left side of the body is facing the imaging element, and a back side body direction in which a back of the body is facing the imaging element. As will be appreciated, any number of body directions and corresponding orientations of the body may be utilized with the disclosed implementation and the four discussed (front side, right side, back side, and left side) are provided only as examples.

In some implementations, the application 125 executing on the portable device 130 may guide the user through different body directions and select one or more 2D images as representative of each body direction. As each 2D body direction image is selected by the application, or after all 2D body direction images are selected, the 2D body direction images are sent from the application 125 executing on the portable device 130 via a network 190 to remote computing resources 103 for further processing. In addition, the user information provided to the application by the user 100 may be sent from the application executing on the portable device 130 to the remote computing resources 103. In other implementations, all processing may be done on the portable device.

The remote computing resources 103 may include a 3D body model system 101 that receives the user information and/or the 2D body direction images and processes those images using one or more neural networks, such as a convolutional neural network, to generate 3D body model parameters corresponding to a dimensionally accurate 3D body model of the body of the user 100 and to compute a body fat measurement value representative of a body fat of the body of the user 100. In addition, one or more of the 2D body direction images, such as a front side 2D body direction image may be processed to determine one or more other body measurements, such as body mass, bone density, height, weight, age, etc.

The 3D body model system 101, upon generating the 3D body model parameters, body fat measurement value and optionally other body measurements, sends the 3D body model parameters, body fat measurement value and any other body measurements back to the application 125 executing the portable device 130. The application 125, upon receipt of the 3D body model parameters, generates from the 3D body model parameters a 3D body model that is representative of the body 100 of the user and presents the 3D body model on a display of the portable device 130. In addition, or instead of generating and presenting the 3D body model, the application may present the body fat measurement value and any other body measurements that are received.

In addition to rendering a 3D body model and presenting the 3D body model, body fat measurement value, and any other body measurements, the user 100 can interact with the presented 3D body model and body measurements. For example, the user may view historical information that was previously collected for the user via the application 125. The user may also interact with the presented 3D body model to rotate and/or turn the presented 3D body model. For example, if the portable device 130 includes a touch-based display, the user may use the touch-based display to interact with the application and rotate the presented 3D body model to view different views (e.g., front, side, back) of the 3D body model.

Figure 2:
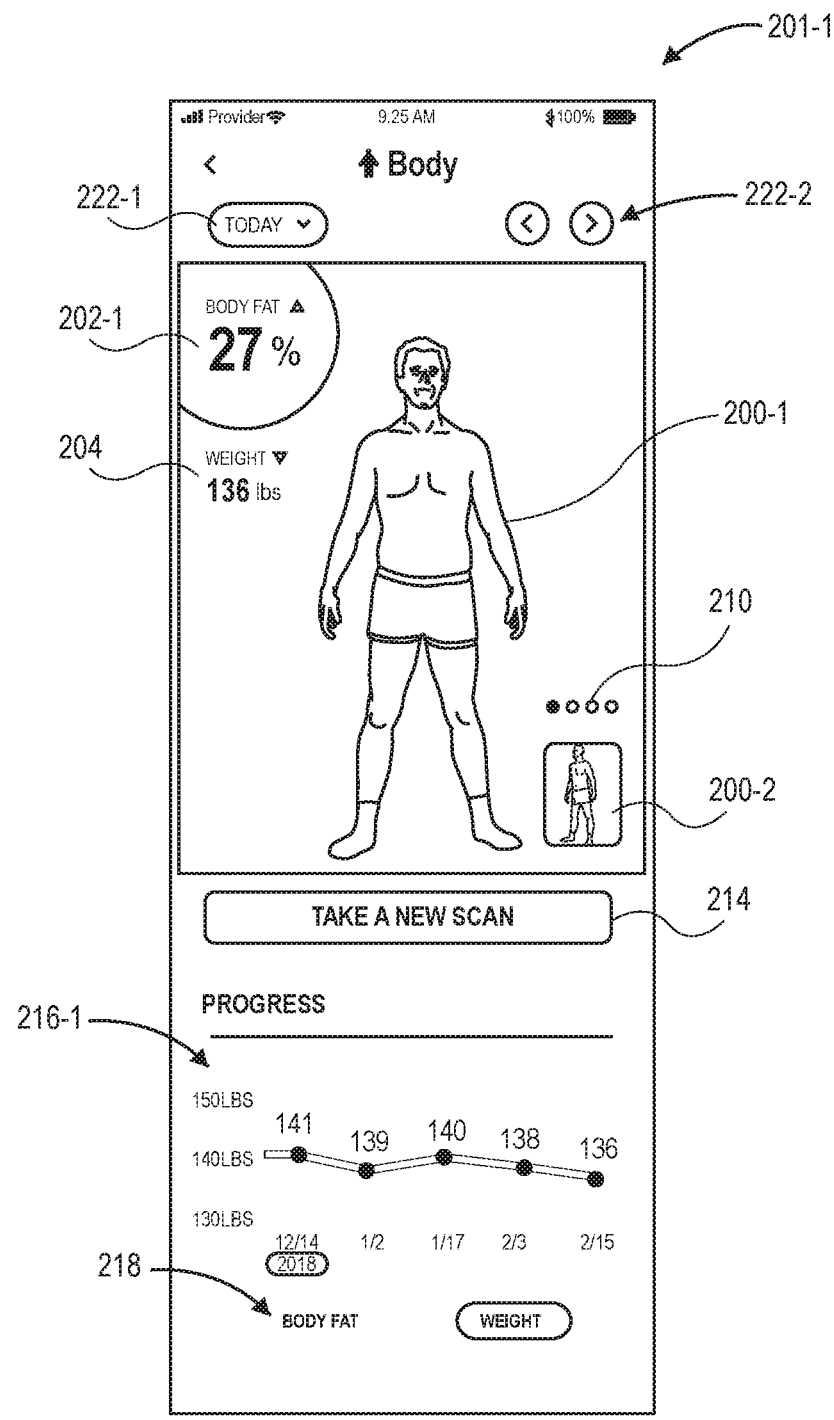
FIG. 2 is a user interface illustrating a captured two-dimensional body image and corresponding body measurement information determined from at least the two-dimensional body image, in accordance with implementations of the present disclosure.

FIG. 2 is a user interface 201-1 presented by an application executing on a portable device, such as the application 125 executing on the portable device 130 discussed above with respect to FIG. 1, in accordance with implementations of the present disclosure.

Figure 3:
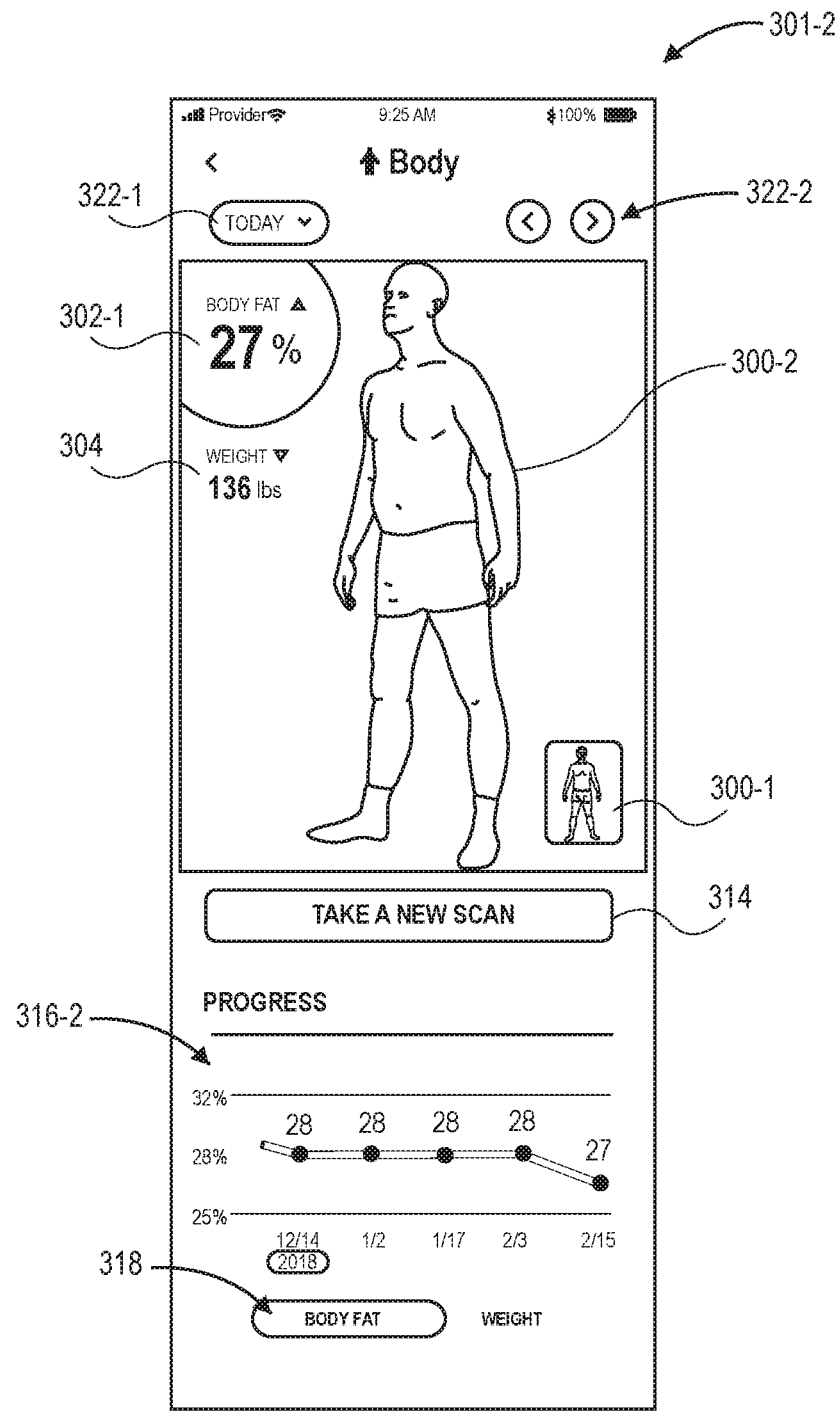
FIG. 3 is a user interface illustrating a three-dimensional body model and corresponding body measurement information generated from a two-dimensional body image, in accordance with implementations of the present disclosure.

In this example, the user interface 201-1 illustrates a 2D body direction image 200-1 captured by an imaging element of the portable device that was used to generate and present a 3D body model, the body fat measurement value 202-1, and other corresponding body measurement information. In this example, the illustrated user interface 201-1 shows the 2D body direction image, the body fat measurement value 202-1, and the weight 204 of the body, which may be determined from the 2D body model image 200-1 and/or provided as user information by the user. In other implementations, additional or fewer body measurements may be presented on the user interface 201-1 by the application. A user interacting with the user interface 201-1 may also select to view other 2D body direction images that were used to generate a 3D body model, body fat measurement value, and/or other body measurements, by selecting the indicators 210 and/or swiping or otherwise indicating with the user interface 201-1 to alter the currently presented 2D body direction image 200-1. The user may also alternate between a view of 2D body direction images 200-1, as illustrated in the user interface 201-1 of FIG. 2 and the rendered and presented 3D body model 200-2, as illustrated in the small image presentation of the 3D body model 200-2 in FIG. 2, and as illustrated as the primary image 300-2 in user interface 301-2 of FIG. 3. Referring briefly to FIG. 3, the user may interact with the application to rotate and/or change the view of the 3D body model 300-2 by directly interacting with the 3D body model 300-2. For example, the user may rotate the presentation of the 3D body model to view different portions of the 3D body model, zoom out to view more of the 3D body model, or zoom in to view details corresponding to a portion of the 3D body model.

In some implementations, if the user has utilized the application over a period of time to generate multiple instances of 3D body models of the user, the user interface may also present historical body measurements 216/316, such as determined body fat measurements, corresponding to the different dates in which 2D body images of the body of the user were captured and used to generate a 3D body model and body measurements of the body of the user. In the illustrated example, the user may select between viewing historical body weight 216-1 illustrated in FIG. 2 and body fat measurement value 316-2, as illustrated in FIG. 3, through selection of the toggle control 218/318. In other implementations, different or additional historical body measurements 216/316 may be accessible through the user interface 201/301.

In addition to viewing historical body measurements 216/316, the user may also access and view either the 2D body images that were collected at those prior points in time and/or view the 3D body models generated from those prior 2D body images, through selection of the date control 222-1/322-1 or the arrow control 222-2/322-2.

Finally, the user may interact with the user interface 201/301 to select to take a new scan of their body by selecting the Take A New Scan control 214/314. In response to a user selecting the Take A New Scan control 214/314, the application executing on the portable device will provide instructions to the user to position the user in the defined pose (e.g., A Pose) and at proper body directions so that 2D body direction images can be generated and used to produce a 3D body model of the body of the user and/or determine a body fat measurement value of the body of the user, as discussed herein.

Figure 4:
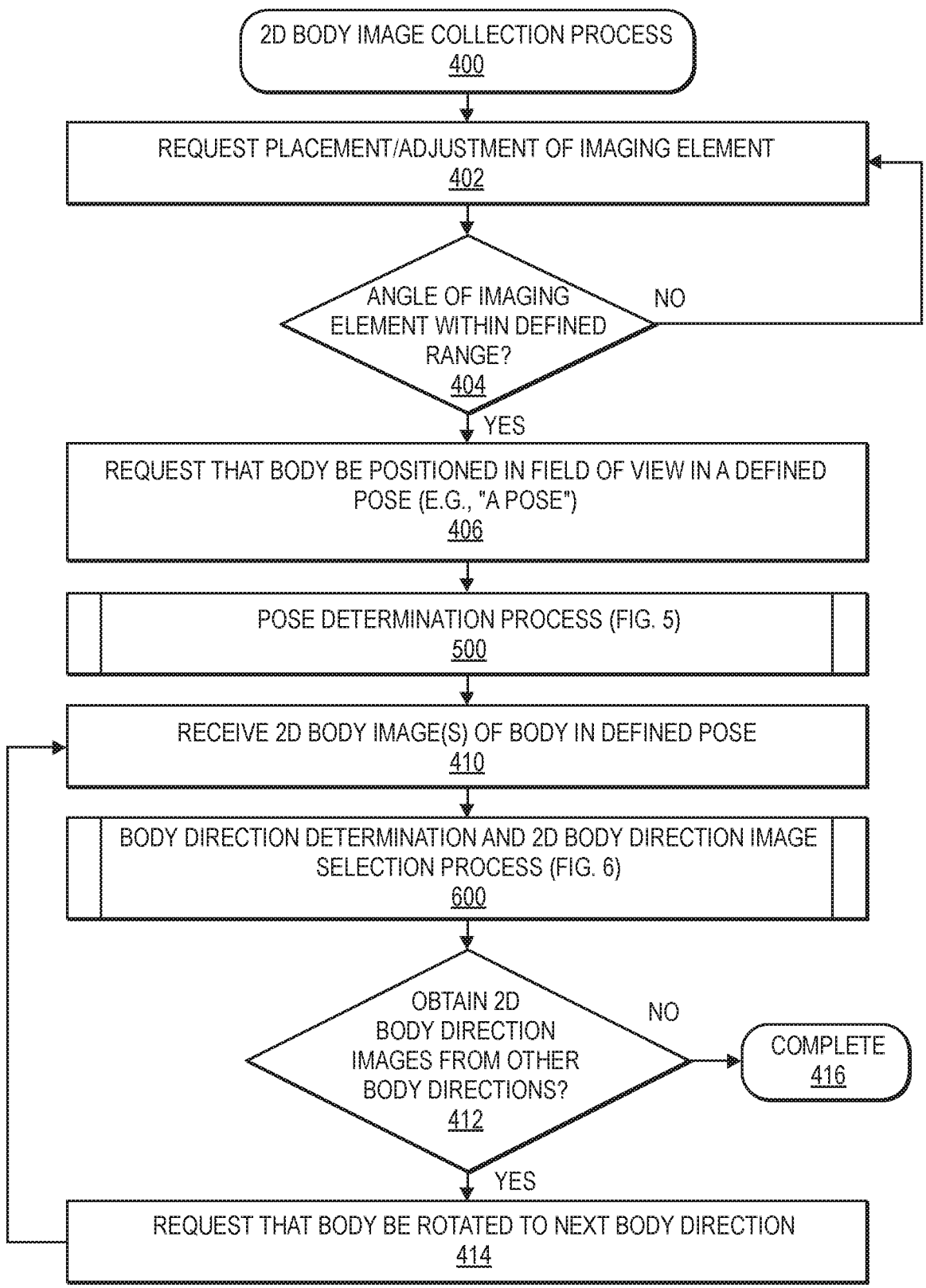
FIG. 4 is an example two-dimensional body image collection process, in accordance with implementations of the present disclosure.

FIG. 4 is an example 2D body image collection process 400, in accordance with implementations of the present disclosure. In some implementations, the example process 400 may be performed by an application executing on a portable device, such as the application 125 executing on the portable device 130 as discussed above with respect to FIG. 1.

The example process 400 begins, for example, when a user interacting with an application executing on a portable device requests to have a 3D body model of their body and/or a body fat measurement representative of a body fat measurement of their body generated. When the process 400 initiates, a request is presented (visually and/or audibly) that an imaging element, such as a camera, or the portable device that includes the imaging element, be positioned at a height, such as between the knees of the body and the head of the body (e.g., between two feet and six feet) and oriented such that the field of view of the portable device is substantially horizontal and oriented toward the body, as in 402. For example, the application executing on the mobile device may present a visual and/or audible output requesting that the portable device be placed within two and five degrees of vertical at about waist height such that the imaging element of the portable device is substantially horizontal and oriented toward the body of the user.

As the imaging element/portable device is placed into position, a determination is made as to whether the angle of the imaging element/portable device is within a defined range, as in 404. For example, data from one or more inputs of the portable device, such as an accelerometer, may be received and processed to determine an angle of the portable device and thus, the angle of the imaging element. The defined range may be any range at which image distortion does not impact the processing of the images to generate the 3D body model, as discussed herein. For example, the defined range may be between zero degrees and ten degrees from vertical. In other implementations, the defined range may be more than zero degrees (e.g., two degrees) to reduce chances of the device falling over due to lack of stability. Likewise, in some implementations the upper bound of the defined range may be less or more than ten degrees. In some instances, the defined range may be greater than or equal to the range or angle indicated in the request to the user for placement of the imaging element/portable device.

If it is determined that the angle of the imaging element is not within the defined range, the example process 400 returns to block 402 and requests adjustment of the imaging element/portable device until the imaging element/portable device is at an angle that is within the defined range.

Once it is determined that the angle of the imaging element/portable device is within the defined range, a confirmation message may be sent to the user and a request may be presented, audibly and/or visually, that the body to be scanned be positioned in the field of view of the imaging element in a defined pose, such as the "A Pose," as in 406. Any defined pose may be requested. When the user is in the A Pose, their arms are slightly separated from their torso and their legs are separated about shoulder width apart such that both their arms and their legs are slightly splayed out diagonally. The A Pose may be particularly beneficial as it separates the body appendages (arms, legs) from each other and from the body core/torso are so that image processing can properly identify and define the parts of the body and body point locations, as discussed further below.

In some implementations, the focal point of the imaging element may also be adjusted based on the position of the body in the field of view of the imaging element. For example, rather than focusing on the entire image, the example process 400 may cause the imaging element to adjust the focal point to focus on the body of the user. Likewise, the exposure of the imaging element may be adjusted based on the lighting of the body of the user within the field of view of the imaging element.

Figure 5:
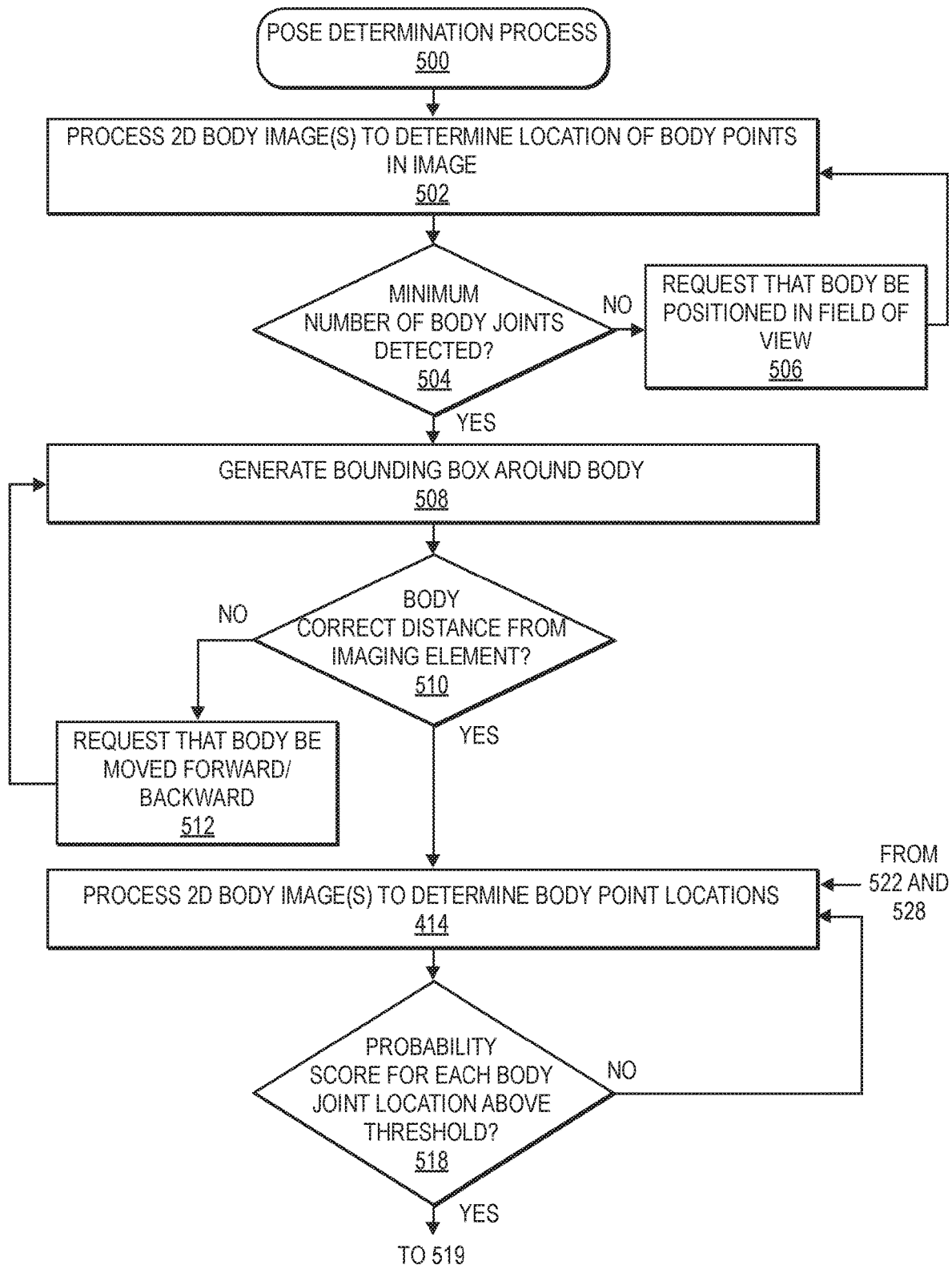
FIG. 5 is an example pose determination process, in accordance with implementations of the present disclosure.
Figure 5:
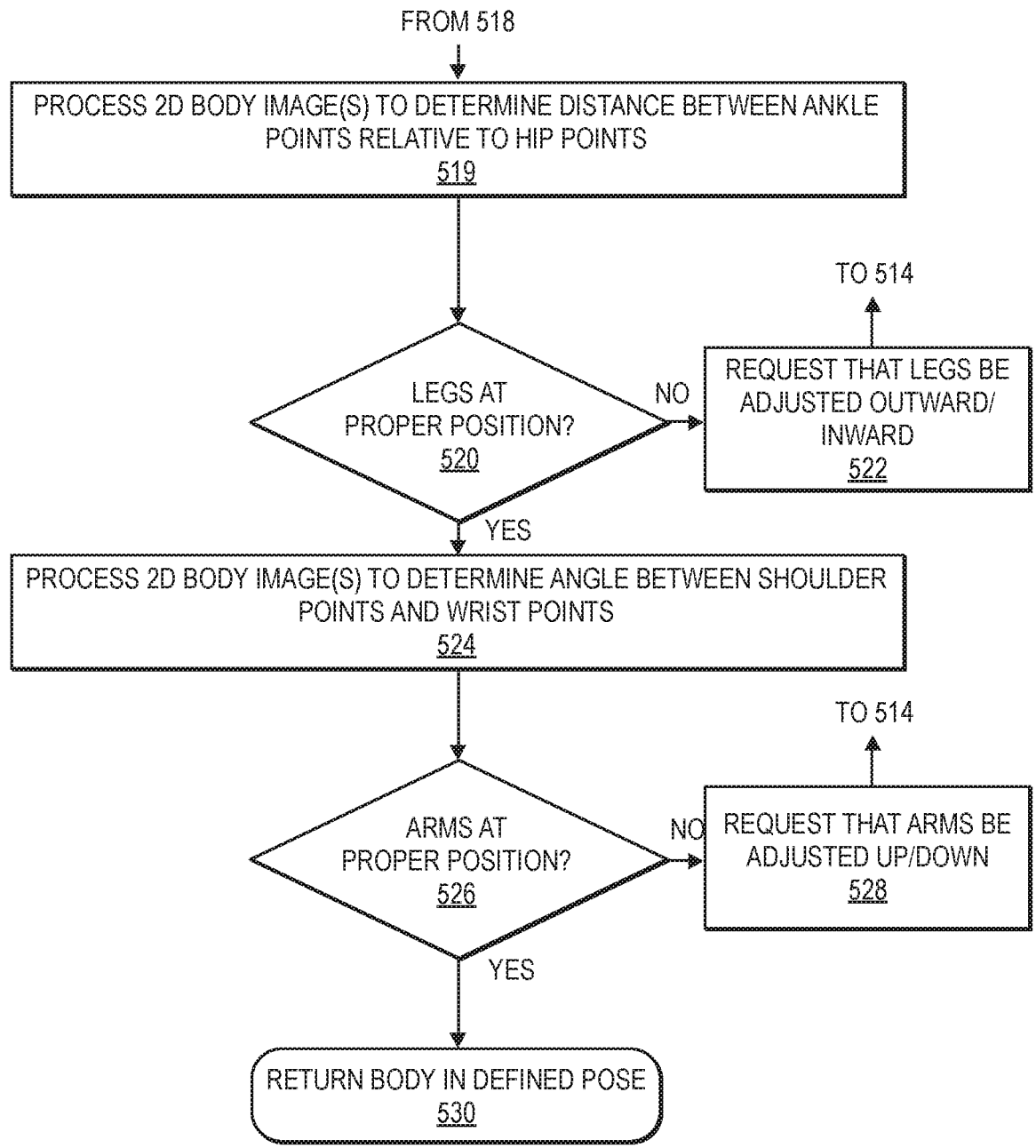

As the request that the user position the body in a defined pose, such as the A Pose, the pose determination process 500 discussed further below with respect to FIG. 5, is performed to confirm that the body is positioned within the field of view of the imaging element and in the defined pose, as in 500. The example process 500 may be performed as illustrated herein at a defined point within the example process 400 to confirm the position and pose of the body before other aspects of the example process 400 are performed. In other implementations, once the example process 500 is initiated, it may continue to monitor the position and pose of the body while the other aspects of the example process 400 are performed. For example, the example process 500, as discussed below, may continue to monitor that the body of the user remains in the field of view and in the defined pose while 2D body images of the body in different body directions are captured, as discussed below. If, during other aspects of the example process 400 it is determined that the body is no longer positioned in the field of view of the imaging element or the body is no longer in the defined pose, the example process 500 may generate a request that the body be positioned in the field of view with the defined pose before other aspects of the example process 400 proceed.

When the example process 500 confirms that the body is within the field of view of the imaging element and in the defined pose, one or more 2D body images of the body in the defined pose are received from the imaging element, as in 410. For example, once it is determined that the body is in the defined pose, one or more images of the user may be obtained by the imaging element of the portable device. Those received images are then processed to determine a body direction of the body and to select a 2D body direction image representative of the body in the determined body direction, as in 600. Body direction determination and 2D body direction image selection are discussed below with respect to FIG. 6 and the example process 600.

Upon completion of the example process 600 in which body direction is determined and one or more 2D body direction images are selected and provided to remote computing resources, a determination is made as to whether additional 2D body direction images of the body from other body directions are to be obtained as part of the example process 400, as in 412. In some implementations, only a single 2D body direction image may be obtained and used to generate 3D body model parameters and/or body measurements. In other implementations, multiple 2D body direction images of the body in different body directions may be obtained with the example process 400 that are used together to generate 3D body model parameters and/or body measurements. For example, in some implementations, four different 2D body direction images (e.g., front side, right side, back side, left side) may be obtained with the example process 400 and used by the remote computing resources to generate 3D body model parameters and/or body measurements. In other implementations, more or fewer than four 2D body direction images may be obtained. In some examples, the user of the application executing on the portable device may select how many 2D body direction images are to be obtained and used for 3D body model parameter generation. In still other examples, body fat measurements may be obtained from images that include less than the entire body of the user. For example, an image that includes one or more legs, one or more arms, a torso, a head, a waist, alone or in combination may be processed with the disclosed implementations and used to generate body fat measurements corresponding to the body of the user.

If it is determined that additional 2D body direction images are to be selected and provided to the remote computing resource for use in generating 3D body model parameters and/or body measurements, a request is presented (e.g., visually and/or audibly) that the body be rotated to a next body direction, as in 414. In some implementations, there may be a defined order in which the body is to be rotated. For example, body direction determination may proceed from front side, to right side, to back side, to left side. Such an order of body direction rotation may aid in the accuracy of body direction determination and distinguishing between left side and right side, or front side and back side.

As the request that the body rotate to a next body direction, the example process 400 returns to block 410 and continues. This portion of the process 400 may continue until all 2D body direction images that are to be used for processing by the remote computing resources have been selected and sent to the remote computing resources. If it is determined at decision block 412 that no additional 2D body direction images are to be obtained, the example process 400 completes, as in 416.

FIG. 5 is an example pose determination process 500, in accordance with implementations of the present disclosure. Similar to the example process 400 (FIG. 4), the example process may be performed by an application executing on a portable device, such as application 125 executing on portable device 130, discussed above with respect to FIG. 1.

As discussed above, the example process 500 may be performed at or near the beginning of the example process 400 to confirm that the body is within the field of view of the imaging element and in the defined pose and then complete. In other implementations, the example process 500 may continually be performed as images are received as part of the example process 400 and 2D body direction images selected.

The example process 500 begins by processing 2D body images received from the imaging element to determine a location of body joints, body features, body parts, etc., generally referred to herein as "body points," in the image, as in 502. For example, each image received from the imaging element may be processed by a neural network, such as a convolutional neural network ("CNN") to determine body point locations, such as the location of body joints (e.g., wrist, ankle, knee), the location of body parts (e.g., hand, foot, shoulder), and/or other body points. As will be appreciated, any trained neural network may be utilized to determine body point locations within a 2D image. In some implementations, because body point determination is performed on the portable device, a low latency neural network, such as ENet may be trained and utilized. In other implementations, other neural networks may be utilized.

The output of the neural network for each image may be a heat map indicating, for each pixel of the image, which is defined by an x, y coordinate (or other coordinate frame), a probability score that a body point is at that position. The probability score may be any defined value or indicator that may be used as in indicator as to the likelihood that a body point has is at the location.

An initial determination may be made as to whether the body is positioned within the field of view of the imaging element by determining if a minimum number of body point locations have been detected with a high enough probability, as in 504. The minimum number may be any defined amount (e.g., one, two, four, etc.). While multiple body points may be located, in some implementations, only particular body points may be considered in determining whether the minimum number of body point locations have been determined.

For example, in some implementations, the body point locations for the left shoulder, right shoulder, left ankle, right ankle, left wrist, right wrist, and top of head may be the only body point locations that are considered when determining that the minimum number of body point locations have been determined.

If it is determined that the minimum number of body point locations have not been detected, a request (e.g., visual and/or audible) may be presented that requests that the body be positioned in the field of view, as in 506. If it is determined that a minimum number of body point locations have been determined, a bounding box is formed around the determined body point locations, as in 508, and a determination made as to whether the body is at an appropriate distance from the imaging element/portable device, as in 510. For example, a determination may be made as to whether the bounding box encompasses a defined amount or percentage range (e.g., 60%-70%) of the image, whether a height of the bounding box is within a defined percentage range (e.g., 70%-80%) or amount of the entire height of the image, whether a width of the bound box is within a defined percentage (e.g., 30%-50%) or amount of the entire width of the image, etc.

If it is determined that the bounding box does not encompass a defined amount of the image, a request (visual and/or audible) may be presented requesting that the body be moved forward or backward with respect to the imaging element/portable device, as in 512, and the example process 500 returns to block 508 and continues. For example, if it is determined that the bounding box does not encompass enough of the image, the request may be a request that the body move closer to the imaging element/portable device. In comparison, if the bounding box encompasses too much of the image, or portions of the body point locations are beyond the image, the request may be a request that the body move farther away from the imaging element/portable device.

Once it is determined at decision block 510 that the body is at a correct distance from the imaging element/portable device, 2D body images received from the imaging element are processed to determine body point locations, as in 514. Processing of the 2D body images to determine body point locations may be performed using the same neural network discussed above with respect to block 502 that is executing on the portable device to determine body point locations of the body positioned in the field of view of the imaging element. As discussed above, the output for each 2D body image processed by the neural network may be a heat map that indicates for each pixel of the 2D body image (in x, y coordinates) a probability that a body point is at that location.

The output (heat map) for each 2D body image may then be considered and a determination made as to whether the probability score for each body point location is above a threshold, as in 518. The threshold may be any value (e.g., 0.7) or indicator and may be different for different body points and/or different body point locations. Likewise, in some implementations, the determination may be for all body point locations indicated by the processing of the 2D body images. In other implementations only the locations and probability scores for select body points may be considered when determining if the probability score has been exceeded for those body point locations. For example, in some implementations, the example process may only consider whether the body point locations for the body points of left shoulder, right shoulder, left ankle, right ankle, left wrist, right wrist, left hip, right hip, and top of head exceed the threshold. In other implementations, fewer or additional body point locations may be considered.

If it is determined that the probability score for each body point location is not above the threshold, the example process 500 returns to block 514 and processes the next 2D body image.

Once it is determined that the body point locations do exceed the threshold, the 2D body image is processed to determine a distance between the location of the left ankle point and the right ankle point relative to the distance between the left hip point and the right hip point, as in 519. For example, it may be determined if the distance between the left ankle point and the right ankle point is equal to or greater than the distance between the left hip point and the right hip point.

Based on the relationship between the distance between the left ankle point and the right angle point relative to the distance between the left hip point and the right hip point, a determination is made as to whether the legs are at a proper position, as in 520. For example, if the defined pose is the A Pose, it may be determined that the legs are in the proper position if the distance between the left ankle point and the right ankle point is greater than or equal to the distance between the left hip point and the right hip point. If the distance between the left ankle point and the right ankle point is not greater than or equal to the distance between the left hip point and the right hip point, it may be determined that the legs are not in a proper position.

If it is determined that the legs are not in a proper position, a request is presented (visually and/or audibly) that the legs of the body be adjusted outward or inward, as in 522. For example, if it is determined that the distance between the left ankle point and the right ankle point is less than the distance between the left hip point and the right hip point, a visual, audible, and/or tactile notification may be presented by the portable device requesting that the legs of the body be separated farther apart. As the request is presented, the example process 500 returns to block 514 and continues until it is determined at decision block 520 that the legs are in the proper position for the defined pose.

Once it is determined at decision block 520 that the legs are in the proper position, the 2D body images are processed to determine an angle between the shoulder points and the wrist points, as in 524. For example, an inverse cosine of normalized dot product may be performed to determine arm spacing based on the locations determined for the left shoulder point, the left wrist point, the right shoulder point, and the right wrist point.

Based on the determined angles between the shoulder points and the wrist points, a determination is made as to whether the left arm and right arm are at the proper position, as in 526. Continuing with the above example, if the defined pose is the A Pose, the proper space of the arms may be such that the angle of the arm formed between the should point and wrist point is between 20 degrees and 40 degrees. In other examples, the arm spacing may be different.

If it is determined that the arms are not at a proper position, a visual, audible, and/or tactile notification may be presented by the portable device requesting that the arms be adjusted up or down, as in 528. For example, if it is determined that the angle of the arms exceed the range for the defined pose, the request may be a request that one or both arms be lowered. In comparison, if it is determined that the angle of the arms is below the range for the defined pose, the request may be a request that one or both arms be raised. As the request is presented, the example process 500 returns to block 514 and continues until it is determined at decision block 526 that the arms are in the proper positioned for the defined pose.

Once it is determined that the arms are in the proper position, the example process 500 returns a notification that the body is in the defined pose (e.g., the A pose), as in 530.

While the above example proceeds in a sequential manner determining that the distance between the body and the imaging element/portable device is correct, the legs are properly positioned, and then the arms are properly positioned, in other implementations, the determination and/or notification for each of the above may be done in parallel or in a different order. Likewise, in some implementations, the requests to make one or more adjustments (e.g., move forward/backward, spread/narrow legs, raise/lower arms) may be presented in any order and/or may all be presented concurrently. In addition, as noted above, the requests may be output by the application executing on the portable device as visual and/or audible outputs. For example, the application may present on a display of the portable device the image of the of the user body as the 2D body images are obtained by the imaging element and overlay a silhouette or other indicator as the proper position for the body according to the defined pose. Specific requests that the user move forward/backward, spread/narrow legs, raise/lower arms may be presented in conjunction with the visual indicators to aid the user in positioning the body in the correct pose.

Figure 6:
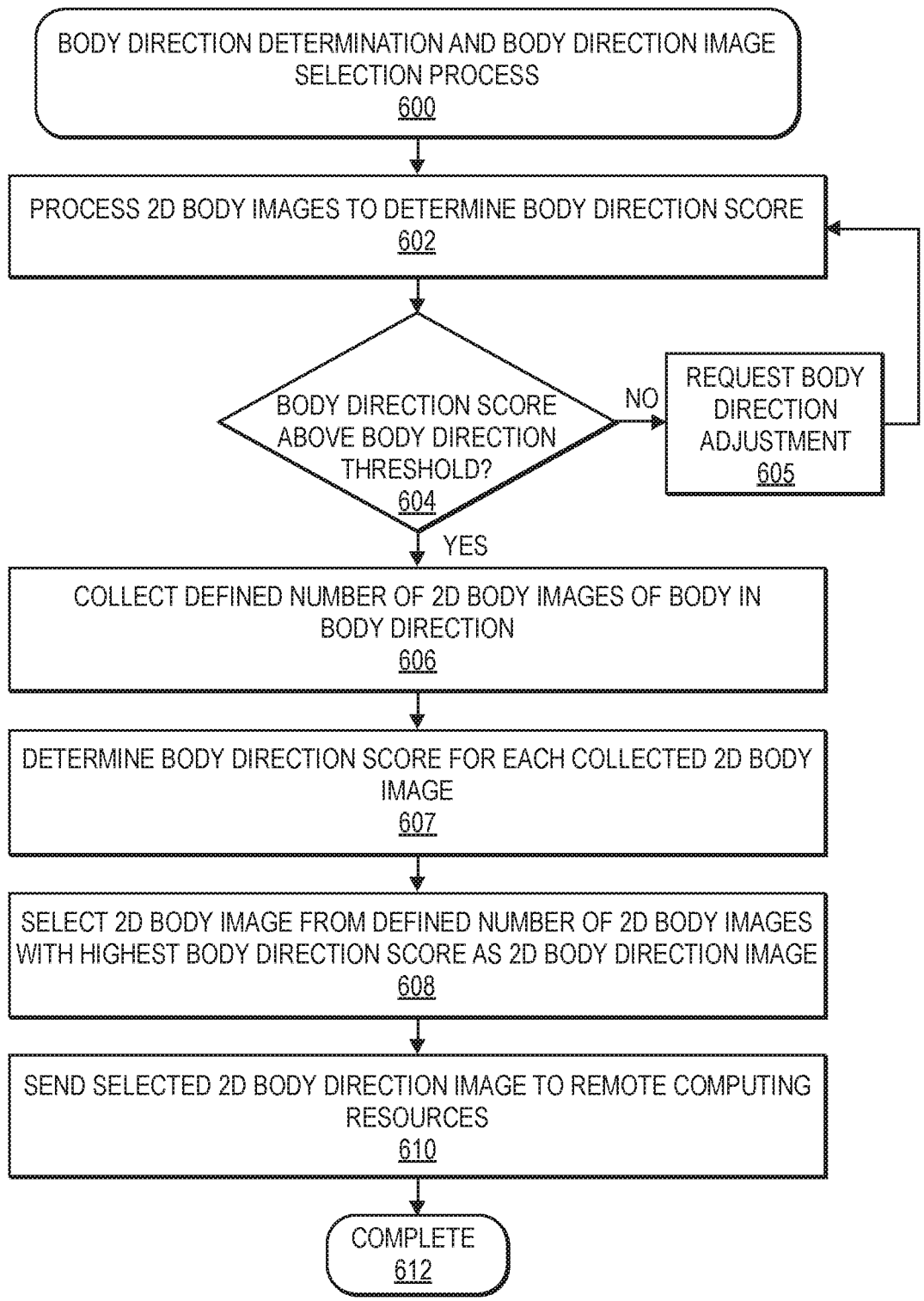
FIG. 6 is an example body direction determination and body direction image selection process, in accordance with implementations of the present disclosure.

FIG. 6 is an example body direction determination and body direction image selection process 600, in accordance with implementations of the present disclosure.

The example process 600 begins by processing 2D body images received from the imaging element of the portable device to determine a body direction score indicative of a direction of the body represented in the 2D body image with respect to the imaging element/portable device, as in 602. Like the example process 400 (FIG. 4) and 500 (FIG. 5), the example process 600 may be performed by the application executing on the portable device. As such, a low latency image processing technique may be performed to determine the body direction of the body represented in the received 2D body images. For example, a low latency neural network, such as a CNN, may be trained to determine a body direction of a body. In one example a MobileNet CNN may be trained to determine a body direction of a body represented in a received 2D body image. In other implementations, multiple CNNs, one for each potential body direction, may be trained to process input 2D body images and output a score indicating a probability that the body represented in the 2D body image corresponds to the body direction for which the CNN was trained. For example, if the example process 400 (FIG. 4) is to obtain 2D body direction images from a front side, right side, back side, and left side, a different CNN may be trained for each of those four body directions. Received 2D body images may be processed in parallel by each of the four CNNs and a body direction score presented by each CNN indicating a probability that the body represented in the 2D body image is in the body direction trained for that CNN. The CNN with the highest score will indicate the likely body direction of the body represented in the 2D body image.

In some implementations, the order of body directions may be controlled by the application and a request may be presented that the body be initially oriented to the front side, then right side, then back side, then left side (or any other order). In such an example, processing requirements may be further reduced by only processing received 2D body images with the CNN trained for the requested body direction. For example, if the request is that the body be oriented in a right side view with respect to the imaging element, a CNN trained for right side body direction detection may be the only CNN executed to process received 2D body images.

As body direction scores are generated, a determination is made as to whether a body direction score for one of the body directions, or a requested body direction, is above a body direction threshold, as in 604. The body direction threshold may be any value or indicator relative to a confidence that the body direction has been accurately determined. If it is determined that the body direction score does not exceed the body direction threshold, a request is presented (visually and/or audibly) that the body be adjusted to the body direction, as in 605. As the request is presented, the example process 600 returns to block 602 and continues.

Once it is determined at decision block 604 that the body direction score for a received 2D body image exceeds the body direction threshold, a defined number of 2D body images of the body in the 2D body direction are collected, as in 606. The defined number of 2D body images may be any defined number (e.g., one, two, five, twenty, fifty, etc.). In addition, a body direction score is computed for each of the collected 2D body images, as in 607. The body direction scores may be computed using the same neural network utilized and discussed above with respect to block 602. For example, if the body direction is determined to be a front view, a CNN trained for front view body directions may be used to determine body directions scores for each of the collected 2D body images.

A 2D body image of the collected 2D body images having a highest body direction score is then selected as the 2D body direction image for that body direction, as in 608. For example, if twenty 2D body images are collected and body direction scores computed by a CNN trained for front view body directions, the 2D body image with a highest body direction score, as determined by the CNN, is selected as the 2D body direction image for the front view body direction.

Finally, the selected 2D body direction image is sent to remote computing resources for processing to generate 3D body model parameters, as in 610, and the example process 600 completes, as in 612. While the illustrated example sends 2D body direction images upon selection, in some implementations, the selected 2D body direction images may remain on the portable device and be sent to the remote computing resources by the example process 400 (FIG. 4) once all 2D body direction images have been selected.

Figure 7:
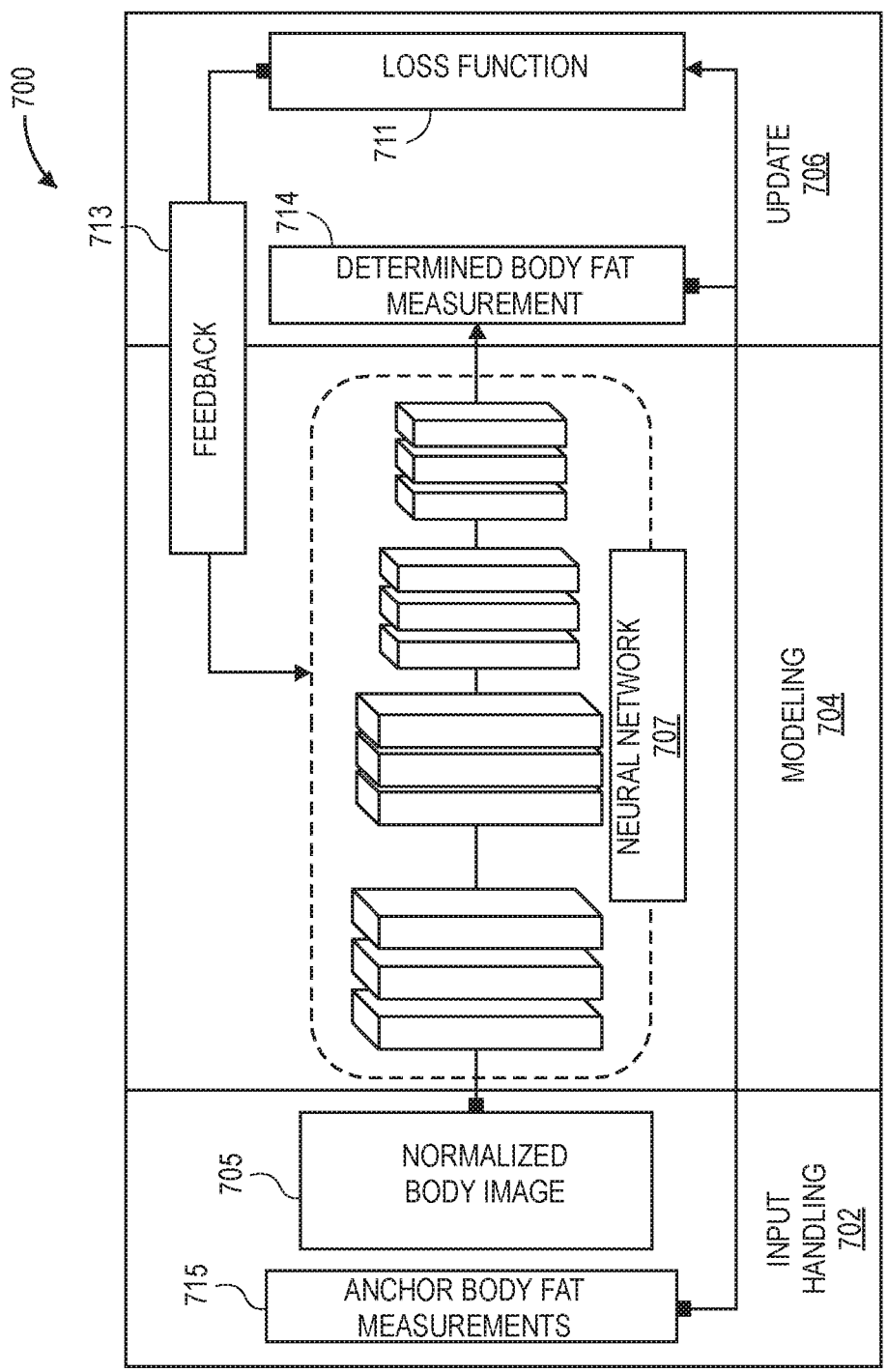
FIG. 7 is a block diagram of an example system operable to determine body fat measurements from a two-dimensional body image, in accordance with implementations of the present disclosure.

FIG. 7 is a block diagram of an example system 700 operable to determine body fat measurements 714 from a 2D body image, in accordance with implementations of the present disclosure. As discussed above, the input 2D body image may include a representation of an entire body or a representation of a portion of the body (e.g., head, torso, leg, arm, head to knee, neck to knee, neck to torso, etc.). Likewise, while the discussions herein focus primarily on receiving and processing a 2D body image, the disclosed implementations may likewise be used with 2D video. In such an implementation, a frame from the video may be extracted and processed with the disclosed implementations to determine body fat measurements for a body represented in the extracted frame.

Each component of the system 700 may be performed as computer executable instructions executing on a computing device, such as the computing resources 103 (FIG. 1) and/or the portable device 130 (FIG. 1). In some implementations, all aspects of the system may execute on one set of computing resources, such as the computing resources 103 or the portable device 130. In other implementations, a first portion of the system 700 may execute on one set of computing resources, such as the portable device 130 while a second portion of the system 700 executes on a second set of computing resources, such as the computing resources 103.

Regardless of the source, the 2D body image is received by an input handling component 702. The input handling component, as discussed in further detail below with respect to FIGS. 9 and 10, processes the received 2D body image and produces a normalized body image 705. The normalized body image is of a defined size, such as 640×256 pixels by 3 channels (red, green, blue). Likewise, pixels that do not represent the body may be suppressed by setting their color values to a defined color, such as black (0,0,0). The normalized body image decreases the number of input variations into the remainder of the system 700.

The normalized body image is then passed to a modeling component 704 that may include one or more neural networks 707. For example, the neural network 707 may be a modified version of a residual network, such as ResNet-50. Residual learning, or a residual network, such as ResNet-50 utilizes several layers or bottlenecks that are stacked and trained to the task to be performed (such as image classification). The network learns several low/mid/high level features at the end of its layers. In residual learning, the neural network 707 is trained to learn the residual of each bottleneck. A residual can be simply understood as a subtraction of the feature learned from input of that layer. Some residual networks, such as ResNet-50 do this by connecting the output of one bottleneck to the input of another bottleneck.

As discussed further below, the disclosed implementations modify the residual network by extracting the features learned in each layer and concatenating those features with the output of the network to determine a body fat measurement value 714 of the body represented in the received 2D body image. The neural network 707 is discussed in further detail below with respect to FIGS. 11 and 12.

In addition to determining a body fat measurement value 714 of the body represented in the 2D image, in some implementations, an update component 706 may be used to determine one or more loss functions 711 from the determined body fat measurements and from anchor body fat measurements 715 that are maintained by the system 700. Anchor body fat measurements, as discussed further below, may be baseline or known body fat measurements for different images, different body parts, body fat measurements corresponding to different body shapes, muscle definitions, etc. The determined loss functions 711 may be fed back into the modeling component 704 and/or directly to the neural network 707 as a feedback 713. The feedback may be used to improve the accuracy of the system 700. Loss functions are discussed in greater detail below with respect to FIG. 13.

In some implementations, additional information may be received by the system 700 and used as additional inputs to the system 700. For example, additional information about the body, such as age, gender, ethnicity, height, weight, etc., may also be received as inputs and used by the neural network 707 in determining a body fat measurement representation and/or a body fat measurement value, as discussed herein.

Figure 8:
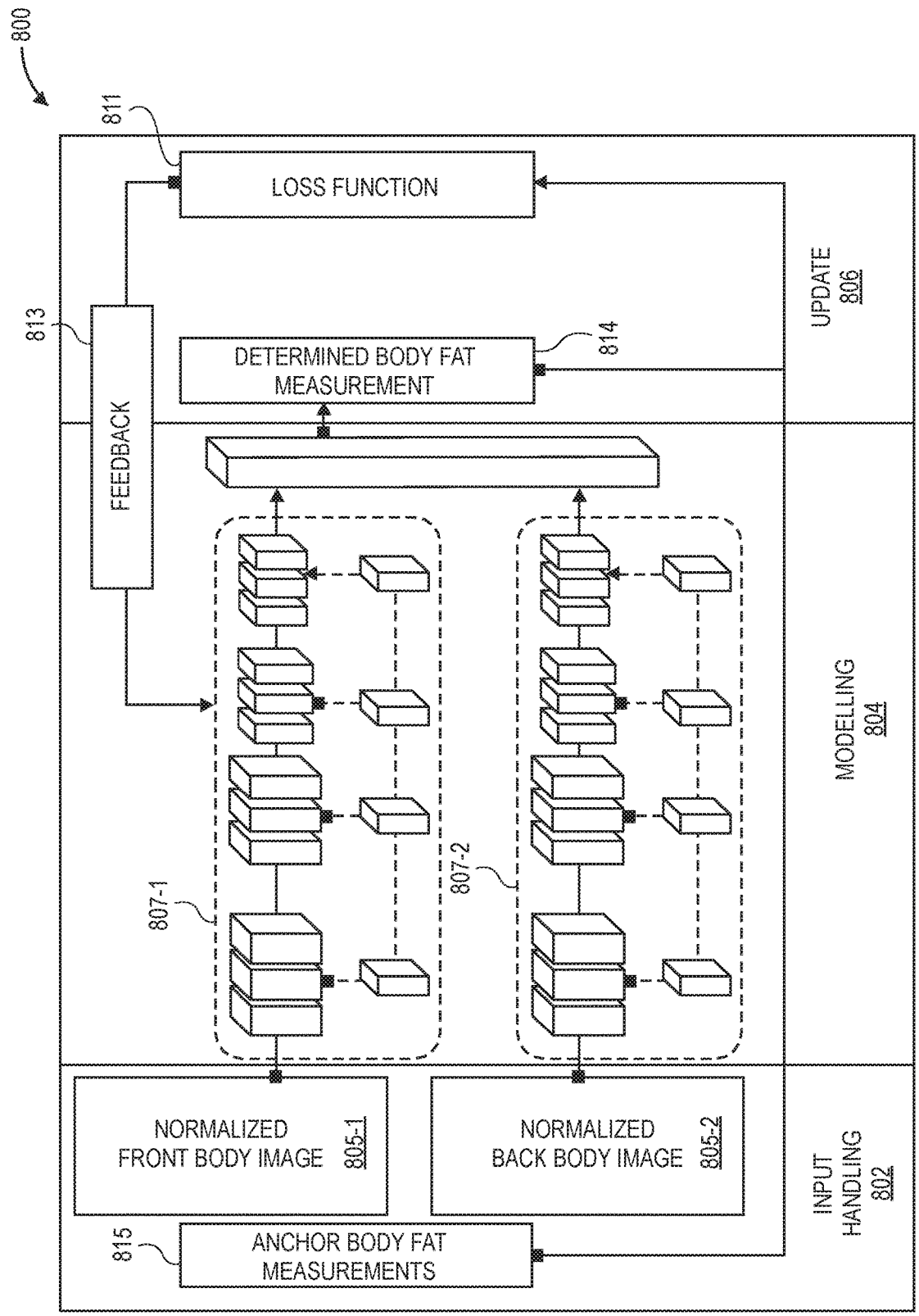
FIG. 8 is a block diagram of an example system operable to determine body fat measurements from multiple two-dimensional body image, in accordance with implementations of the present disclosure.

FIG. 8 is a block diagram of another example system 800 operable to determine body fat measurements from multiple 2D body images, in accordance with implementations of the present disclosure.

In the example illustrated in FIG. 8, multiple input images are received by the input handling component 802 and each image is processed, as discussed below, to generate respective normalized body images. For example, if a first image is a front side view image, the front side view image may be processed by the input handling component 802 to produce a normalized front body image 805-1. Likewise, if the second image is a back side view image, the back side view image may be processed by the input handling component 802 to produce a normalized back body image 805-2.

Each normalized body image 805 is passed to the modeling component 804 and processed by one or more neural networks, such as neural network 807-1 or neural network 807-2 to determine respective body fat measurement values. The outputs of those processes may be combined to produce a single body fat measurement value 814 representative of the body represented in the input images.

In addition, the determined body fat measurement may be processed by an update component 806 along with anchor body measurements 815 to determine one or more loss functions 811 that are provided as feedback 813 to the modeling component and/or the neural networks 807 to improve the accuracy of the system 800. In some implementations the final body fat measurement value 814 may be processed by the update component 806 to determine the loss functions. In other implementations, the determined body fat measurement representations determined for each of the normalized body images may be individually processed by the update component 806 and the respective loss function provided as feedback 813 to the respective portion of the modeling component and/or the neural network that processed the normalized body image. For example, the update component may determine a first loss function based on the determined body fat measurement generated by the neural network 807-1 and provide first loss functions as first feedback to the neural network 807-1. Likewise, the update component 806 may also determine a second loss function based on the determined body fat measurement generated by the neural network 807-2 and provide the second loss functions as second feedback to the neural network 807-2.

In still other examples, rather than utilizing a single neural network to process each received normalized input image, neural networks may be trained to process a combination of normalized input images to determine a body fat measurement value. For example, if the combination of front side view body image and back side view body image is often received, a single neural network may be trained to process both normalized body images concurrently to determine a body fat measurement value from the two images. In other implementations, other combinations of images, body directions in the images, or number of images may likewise be used to train a neural network for processing those images and determining a body fat measurement for the body represented in those images.

In some implementations, additional information may be received by the system 800 and used as additional inputs to the system 800. For example, additional information about the body, such as age, gender, ethnicity, height, weight, etc., may also be received as inputs and used by the neural networks 807 in determining a measured visual body fat representation and/or a body fat measurement value, as discussed herein.

In some implementations, the system 700/800 may also produce other outputs in addition to the body fat measurement representations and/or body fat measurement values. For example, in some implementations, the disclosed implementations may also produce information indicating the age, gender, ethnicity, body mass index, height, weight, body dimensions (e.g., arm length, waist circumference, leg circumference, etc.).

Figure 9:
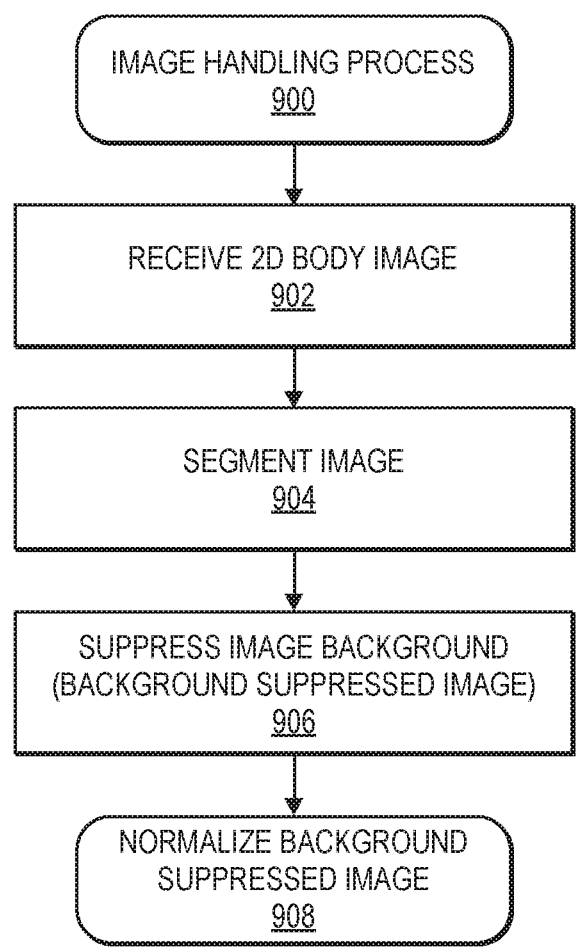
FIG. 9 is an example two-dimensional body image handling process, in accordance with implementations of the present disclosure.

FIG. 9 is an example 2D body image handling process 900, in accordance with implementations of the present disclosure. The example process 900 may be performed by the input handing component 702/802 discussed above in FIGS. 7 and 8.

The example process 900 begins upon receipt of a 2D body image, as in 902. The 2D body image may be received directly from a 2D camera or may be one of the 2D body images selected from the body direction determination and body direction image selection process 600 (FIG. 6) discussed above.

Regardless of the source, the received 2D body image is segmented and the pixels that correspond to a background are suppressed to isolate the body represented in the image and produce a background suppressed image, as in 904 and 906. For example, referring now to FIG. 10, input image 1010, which in this example is a 2D body image 1001, may be processed to segment 1012 pixels of the image that represent the body 1000 from pixels of the image that do not represent the body, referred to herein as background 1002-1/1002-2 pixels, to produce an image that only includes a representation of the body 1000, as represented in the segmented image 1003. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the body. The background pixels may be assigned RGB color values for black (i.e., 0,0,0).

In another example, a neural network utilizing a semantic segmentation algorithm may be trained using images of bodies, such as human bodies, or simulated human bodies to train the neural network to distinguish between pixels that represent human bodies and pixels that do not represent human bodies. In such an example, the neural network may process the received image 1001 and indicate or label pixels that represent portions of the body, such as hair, body, hands, feet, upper-clothing, lower-clothing, and pixels that do not represent the body (background). The background pixels 1002-1/1002-2 may be assigned RGB color values for black (i.e., 0,0,0).

In other implementations, other forms or algorithms, such as edge detection, shape detection, etc., maybe used to determine pixels of the image that represent the body and pixels of the image that do not represent the body and pixels that do not represent the body suppressed.

Returning to FIG. 9, the background suppressed image is then normalized to produce a normalized body image, as in 908. Referring again to FIG. 10, background suppressed image 1003 is normalized 1014 to produce a normalized body image 1005 that is of a defined size, such as 640×256 pixels, with three channels (Red, Green, Blue). Producing the normalized body image may include rescaling the body 1000 to fill a bounding box of the defined size and then setting the normalized body image to that bounding box so that the body is resized and centered in the image.

Figure 11:
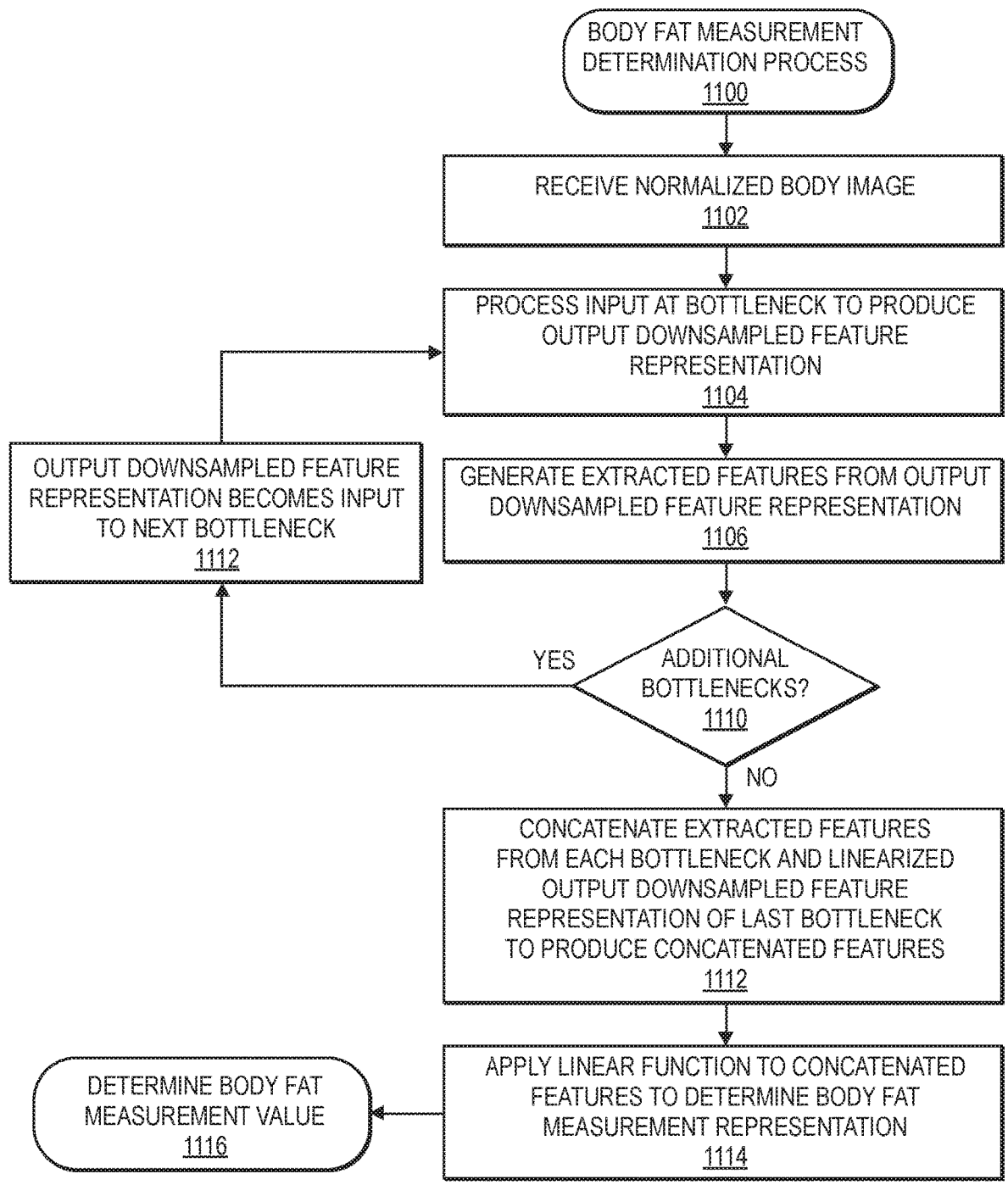
FIG. 11 is an example body fat measurement determination process, in accordance with implementations of the present disclosure.

FIG. 11 is an example body fat measurement determination process 1100, in accordance with implementations of the present disclosure. The example body fat measurement determination process may be performed by the modeling component 704/804 (FIGS. 7 and 8) discussed above. For example, the body fat measurement determination process 1100 may be performed by the modified neural network 707/807 discussed above.

Figure 10:
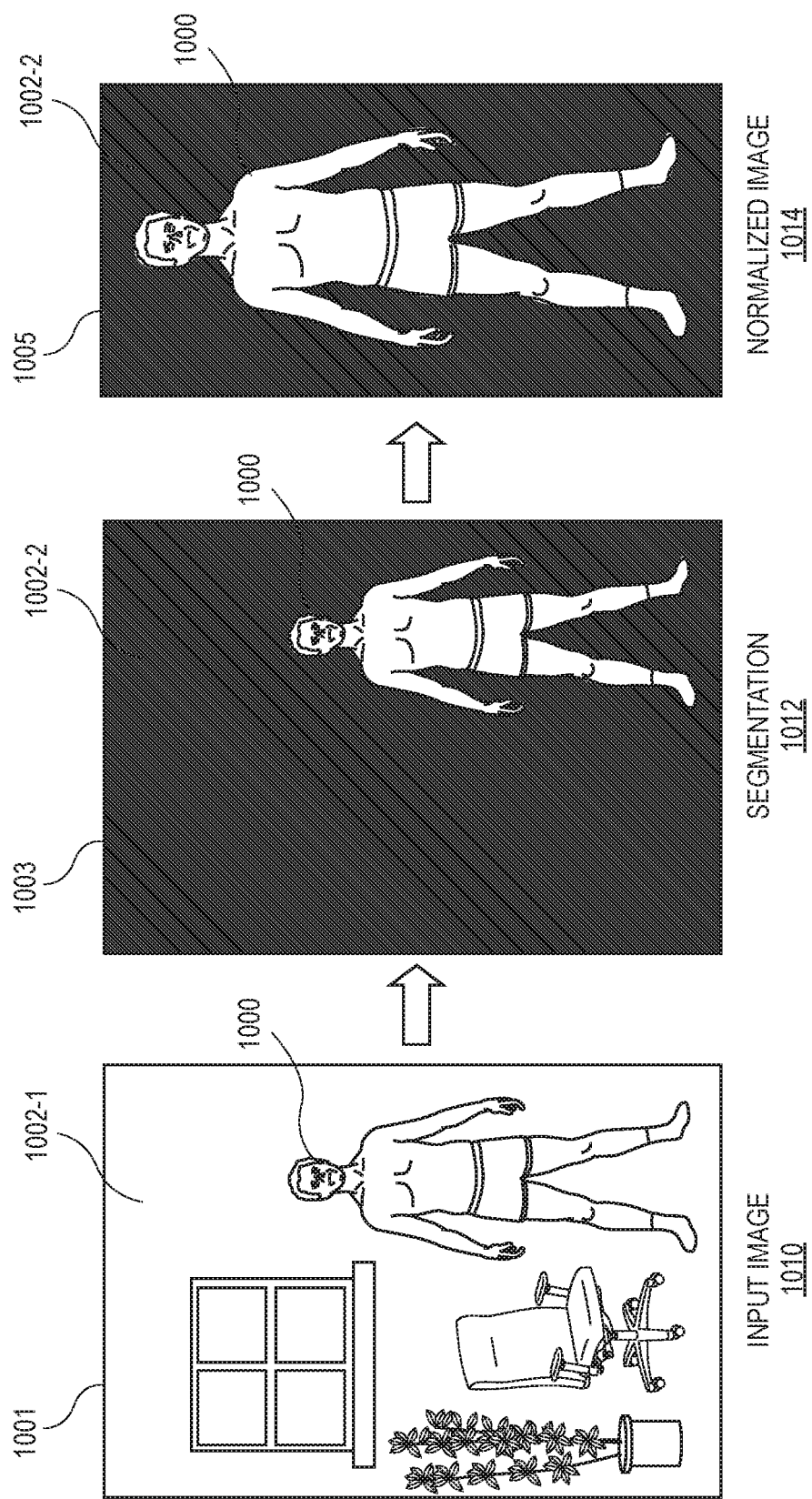
FIG. 10 is an example of image handling of a two-dimensional body image, in accordance with implementations of the present disclosure.

The example process 1100 begins upon receipt of the normalized body image, as in 1102. The normalized body image may be, for example, the normalized body image produced from the example process 1000 (FIG. 10).

The normalized body image is processed as an input to a first bottleneck of the neural network and the first bottleneck outputs a downsampled feature representation, as in 1104. For example, referring to FIG. 12, illustrated is an example system 1200 that includes a neural network 1207 configured to determine body fat measurements from a normalized 2D image, in accordance with implementations of the present disclosure.

Figure 12:
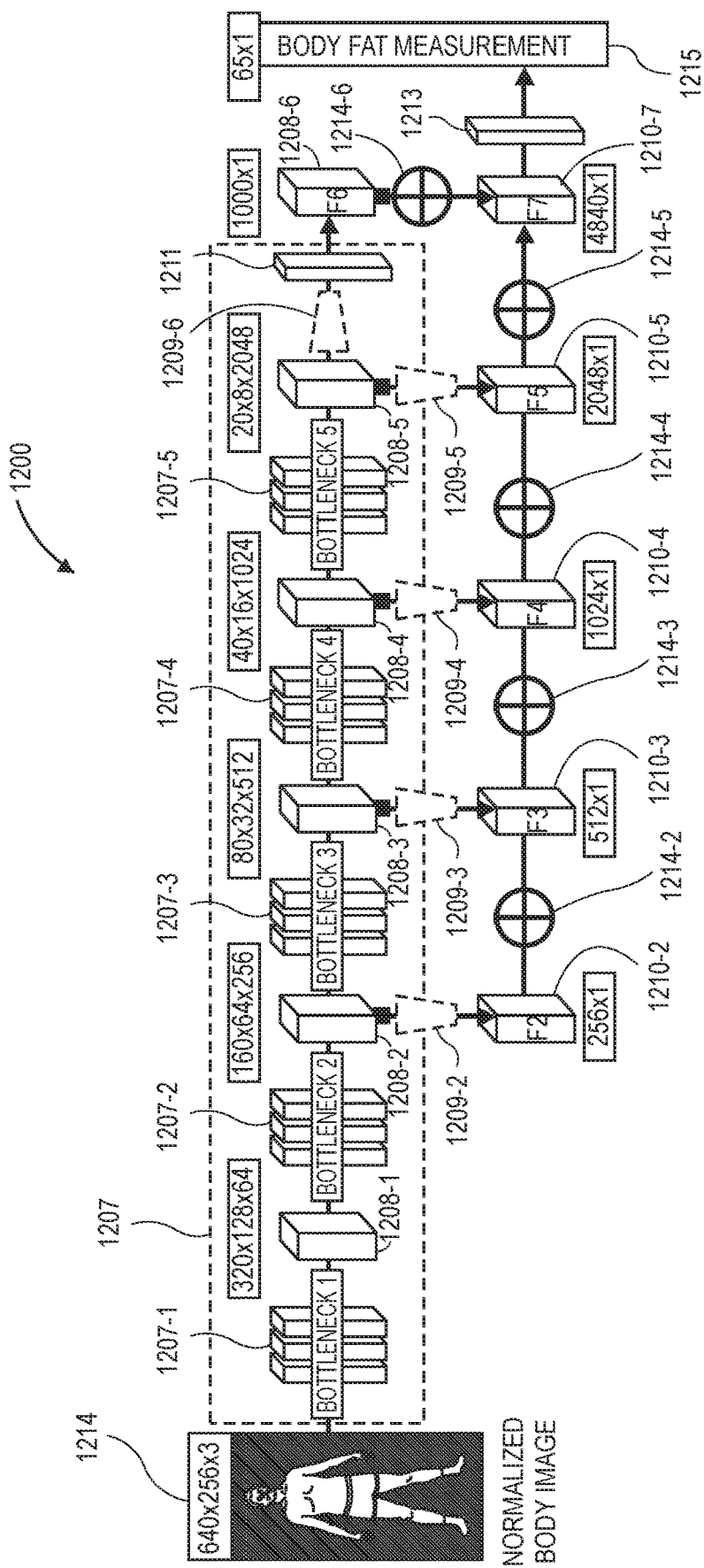
FIG. 12 is an example neural network configured to determine body fat measurements from a normalized two-dimensional image, in accordance with implementations of the present disclosure.

FIG. 12 illustrates an example neural network, such as ResNet-50, modified as discussed herein. In the illustrated example, the neural network 1207 includes five bottlenecks 1207-1, 1207-2, 1207-3, 1207-4, and 1207-5, each of which process an input and generate a downsampled feature representation as an output. Each bottleneck is a stack of deep-learning units, such as convolution layers, non-linear activation functions (Rectified Linear Units ("ReLU")), pooling operations (MaxPooling, Average Pooling) and batch normalization.

In the illustrated example, each bottleneck 1207-1 through 1207-5 reduces the spatial resolution of the input by a factor of two. In other implementations, the spatial resolution may be downsampled differently.

The first bottleneck 1207-1 receives the normalized body image 1214 as the input and reduces the spatial resolution of the normalized body image from 640×256, by a factor of two, down to 320×128. Likewise, in this example, the channels are increased to 64 channels. In other implementations, channel increase may be different based on, for example, computing capacity, computation time, etc. Accordingly, in this example, the output of the first bottleneck 1207-1 is a feature representation 1208-1 with a height of 320, a width of 128, and 64 channels.

Referring back to FIG. 11, the example process 1100 then generates extracted features from the downsampled feature representation, as in 1106. For example, the features from any one or more bottlenecks may be extracted by averaging the outputs of the bottleneck across the spatial dimensions. For example, referring again to FIG. 12, if the features are extracted from the output 1208-1 of the first bottleneck 1207-1, the 64 feature channels are averaged across the 320×128 spatial dimensions to get $F_1 \in 64 \times 1$. In some implementations, features may not be extracted from all bottlenecks of the neural network. For example, as illustrated in FIG. 12, features may not be extracted from the first output of the first bottleneck 1207-1 for use in determining the body fat measurement. In other examples, features may not be extracted from other bottlenecks of the neural network. In comparison, in some implementations, features may be extracted from all bottleneck outputs and utilized with the disclosed implementations.

As the features are extracted, a determination is made as to whether additional bottlenecks remain to be processed, as in 1110. If it is determined that additional bottlenecks remain, the downsampled feature representation from the upstream bottleneck is used as the input to the next bottleneck, as in 1112, and the process 1100 continues.

For example, referring again to FIG. 12, the first downsampled feature representation 1208-1 output from the first bottleneck 1207-1 is provided as an input to the second bottleneck 1207-2. The second bottleneck 1207-2 receives the first downsampled feature representation 1208-1, which has spatial dimensions of 320×128, and 64 channels and processes that input to produce a second downsampled feature representation 1208-2 that has spatial dimensions of 160×64 and 256 channels. As the example process 1100

(FIG. 11) continues, the third bottleneck 1207-3 receives the second downsampled feature representation 1208-2 and processes that input to produce a third downsampled feature representation 1208-3 that has spatial dimensions of 80×32 and 512 channels. The fourth bottleneck 1207-4 receives the third downsampled feature representation 1208-3 and processes that input to produce a fourth downsampled feature representation 1208-4 that has spatial dimensions of 40×16 and 1024 channels. The fifth bottleneck 1207-5 receives the fourth downsampled feature representation 1208-4 and processes that input to produce a fifth downsampled feature representation 1208-5 that has spatial dimensions of 20×8 and 2048 channels.

As illustrated in the example process 1100 and the system 1200, extracted features 1210 are generated from the output downsampled feature representations, as in 1106. For example, continuing with the discussion of FIG. 12, the 256 channels of the second downsampled feature representation 1208-2 may be averaged 1209-2 across the 160×64 spatial dimensions to get second extracted features 1210-2 $F_2 \in 256 \times 1$. The 512 channels of the third downsampled feature representation 1208-3 may be averaged 1209-3 across the 80×32 spatial dimensions to get third extracted features 1210-3 $F_3 \in 512 \times 1$. The 1024 channels of the fourth downsampled feature representation 1208-4 may be averaged 1209-4 across the 40×16 spatial dimensions to get fourth extracted features 1210-4 $F_4 \in 1024 \times 1$. The 2048 channels of the fifth downsampled feature representation 1208-5 may be averaged 1209-5 across the 20×8 spatial dimensions to get fifth extracted features 1210-5 $F_5 \in 2048 \times 1$.

In addition to the extracted features 1210-2 through 1210-5 (i.e., $F_1$ through $F_5$) extracted from each downsampled output, a neural network output feature may also be generated based on an output of the neural network 1200. For example, block 1209-6, which corresponds to block 1209-5, may output an average of the fifth downsampled feature representation 1208-5. A linear function 1211 may be applied to the output to produce a 1000-channel feature 1208-6 $F_6$.

Returning to FIG. 11, if there are no additional bottlenecks to process, the example process 1100 utilizes a multiscale representation which combines the extracted features from each of the downsampled inputs and concatenates them with the 1000-channel feature output from the neural network to produce concatenated features, as in 1112.

Referring again to FIG. 12, as features 1210-2 through 1210-5 are extracted or after all have been extracted, the features are concatenated. For example, $F_2$ 1210-2 is concatenated with $F_3$ 1210-3, which is concatenated with $F_4$ 1210-4, which is then concatenated with $F_5$ 1210-5, as illustrated by concatenation indicators 1214-2, 1214-3, 1214-4. The concatenation of features $F_1$ through $F_5$ is also concatenated with the feature $F_6$ output from the neural network 1207, as indicated by concatenation indicators 1214-5 and 1214-6 to produce concatenated features 1210-7 $F_7 = [F_2, F_3, F_4, F_5, F_6] \in 4840 \times 1$.

A linear function may then be applied to the concatenated features to determine a body fat measurement representation, as in 1114 (FIG. 11). For example, as illustrated in FIG. 12, linear function 1213 may be applied to $F_7$ 1210-7 to produce a determined body fat measurement representation 1215 which, in this example is a 65×1 dimensional vector. For example, the determined body fat measurement representation ("V") 1215 may be determined as:

$$V = W \times F_7 + B \in 65 \times 1$$

where $W \in 65 \times 4840$ and $B \in 65$ are weights and bias of a linear function which my be implemented as a matrix product $W \times F_7$ and summed with the bias matrix B. The weights may be different for each feature $F_1$ through $F_5$ and may be applied as part of the extraction and averaging 1209, or as part of the vector representation of the body fat measurement representation. In other implementations, no weights may be applied.

As illustrated, the above determines a 65-dimensional measured body fat representation $V \in 65 \times 1$ in which each element $V_j$, $j \in \{0, \ldots 64\}$ denotes the probability of the body fat measurement being j. This body fat measurement representation 1215 may then be further processed to determine a body fat measurement value, as in 1116. For example, a probability weighted average of V, namely $\hat{V} = \Sigma_j j V_j$, may be determined and used as the body fat measurement value ("$\hat{V}$"). For example, if the neural network 1207 determines that the probability of the body fat measurement being 22 is 0.5, the probability of the body fat measurement being 23 is 0.5, and all other probabilities are 0:

$$V = 22 \times 0.5 + 23 \times 0.5 = 22.5$$

Figure 13:
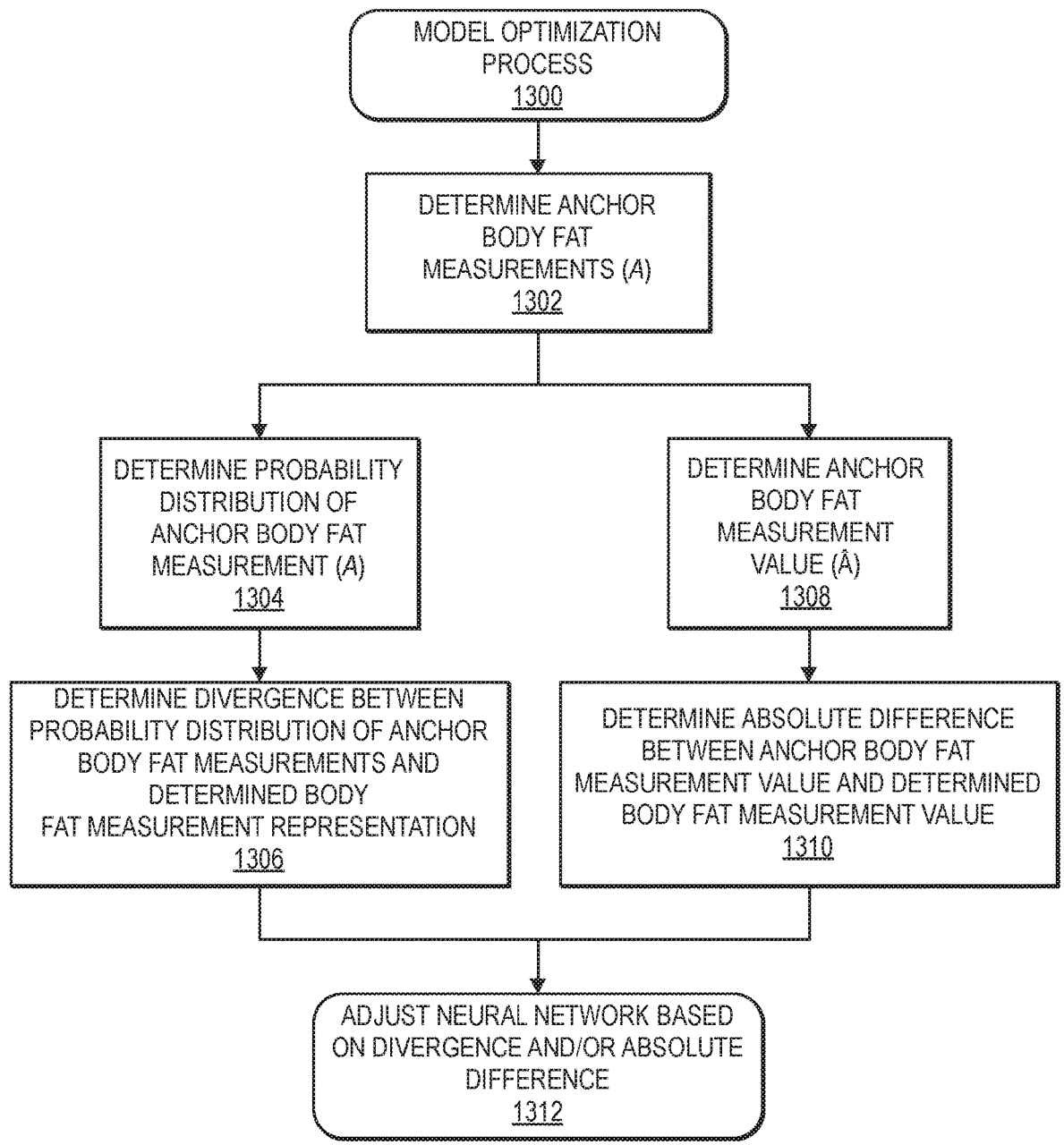
FIG. 13 is an example model optimization process, in accordance with implementations of the present disclosure.

FIG. 13 is an example model optimization process 1300, in accordance with implementations of the present disclosure. As discussed above, in some implementations the determined body fat measurement representation or the body fat measurement value may be compared to known or anchor body fat measurement representation or anchor body fat measurement values to determine loss functions and those loss functions may be provided back to the neural network to improve the accuracy of the neural network and the resultant body fat measurements.

The example process 1300 begins by determining anchor body fat measurements ("A"), as in 1302. The anchor body fat measurements may be vector based body fat measurements representations and/or body fat measurements values. The anchor body fat measurements may be obtained from human annotators that are trained to determine body fat measurements for bodies represented in images, obtained from other systems that measure body fat of a body (e.g., DEXA, ADP), and/or obtained from other sources. In some implementations, the anchor body fat measurements may be an average of multiple body fat measurements of a body obtained from different sources. For example, if there are N human annotators that have determined the body fat of a particular body to be $a_1, a_2, a_3 \ldots a_N$ an anchor body fat measurement may be determined for the body as an average of those determination $$\hat{A} = \frac{1}{N} \sum_n a_n.$$

Likewise, to determine an anchor probability distribution, a probability distribution may be determined based on the body fat measurements provided by the annotators themselves. For example, if four annotators determine the body fat measurement of the body to be 20, 21, 21, 22, the probability distribution may be determined to be $A_{20} = 0.25$, $A_{21} = 0.5$, $A_{22} = 0.25$, and $A_n = 0$, $\forall n \notin \{20, 21, 22\}$. As another example, the body fat measurements may be fit to a Gaussian probability distribution that is centered about the average body fat measurement and decays as it moves away from the average. The peak location and the rate of decay may be controlled by varying the mean and sigma parameters μ, σ.

Returning to FIG. 13, in this example, two loss functions, a KL-Divergence and a Smooth L1 loss may be computed. Computation may be done in parallel, as illustrated, or in series. Likewise, in other implementations fewer, additional, and/or different loss functions may be computed and used to update the parameters of the neural networks to improve the operation thereof and continue to increase the accuracy of the resultant visual body fat measurements.

For the KL-Divergence, a probability distribution of the anchor body fat measurements is determined, as in 1304. The probability distribution of the anchor body fat measurements may be determined as discussed above.

A divergence between the probability distribution of the anchor body fat measurement and the determined body fat measurement representation is then determined, as in 1306. As discussed above, the determined body fat measurement representation may be a 65-dimensional vector that represents the probability distribution of the body fat measurement determined in accordance with the above disclosed implementations.

An anchor body fat measurement value ("Â") may also be determined for the anchor body fat measurements, as in 1308. As discussed above, the body fat measurement value may be an average of the body fat measurements for the body received from different sources. The smooth L1 loss, also known as a Huber Loss, is an unsigned difference between the anchor body fat measurement value ($\hat{A}$) and the determined body fat measurement value ($\hat{V}$), or $|\hat{V}-\hat{A}|$, as in 1310.

Finally, the neural network may be adjusted based on the computed loss functions, in this example the divergence and the absolute difference, as in 1312.

Figure 14:
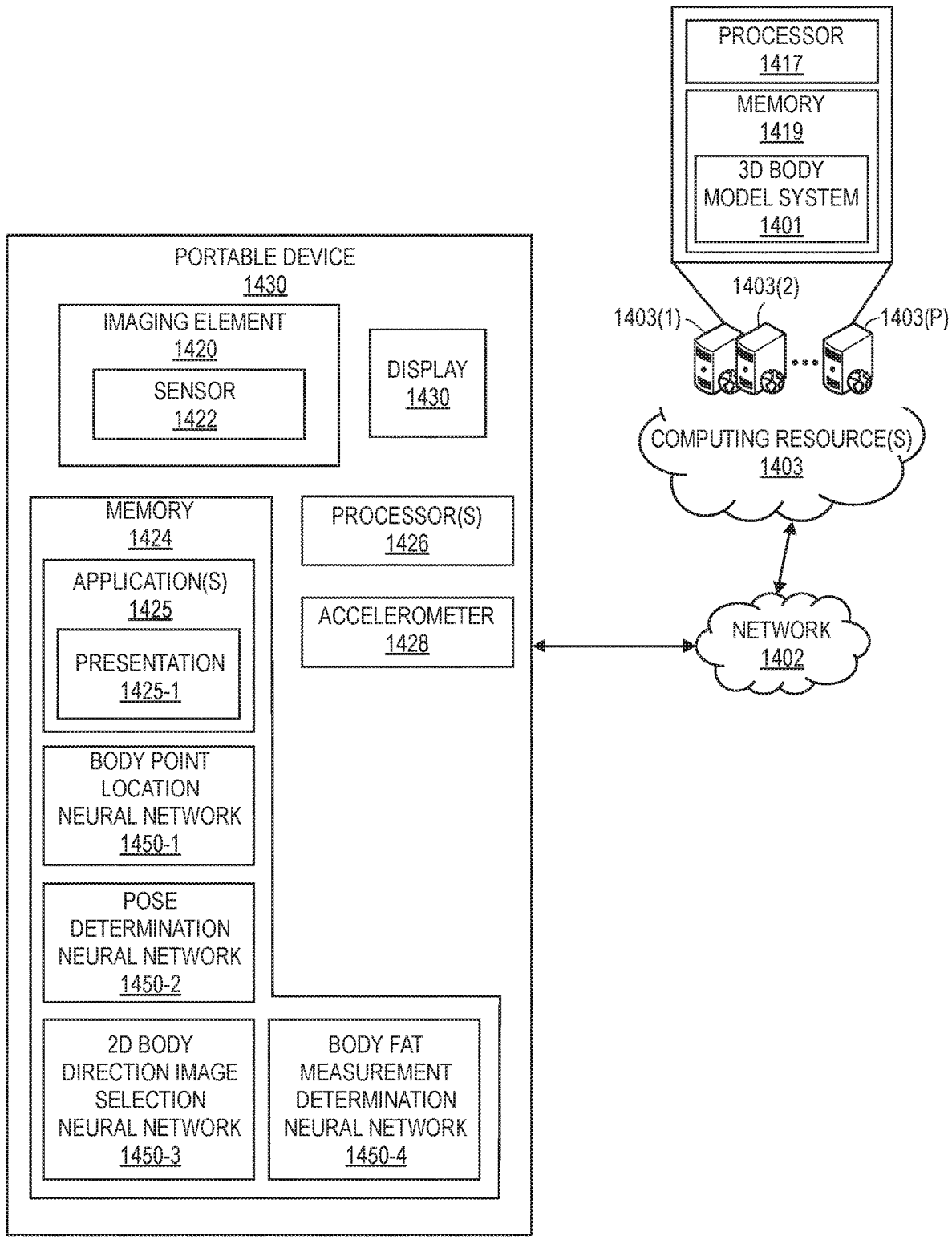
FIG. 14 is a block diagram of example components of a portable device and remote computing resources, in accordance with implementations of the present disclosure.

FIG. 14 is a block diagram of example components of a portable device 1430 and remote computing resources 1403, in accordance with implementations of the present disclosure.

As illustrated, the portable device may be any portable device 1430 such as a tablet, cellular phone, laptop, wearable, etc. The imaging element 1420 of the portable device 1430 may comprise any form of optical recording sensor 1422 or device that may be used to photograph or otherwise record information or data regarding a body of the user, or for any other purpose. As is shown in FIG. 14, the portable device 1430 is connected to the network 1402 and includes one or more memory 1424 or storage components (e.g., a database or another data store), one or more processors 1426, an accelerometer 1428 or other position/orientation/angle determining component, an output, such as a display 1430, speaker, haptic output, etc., and any other components that may be required in order to capture, analyze and/or store and/or transmit imaging data, such as the 2D body images discussed herein and/or to receive 3D body model parameters and/or body measurements and to render and present a 3D body model and/or body fat measurement. For example, the imaging element 1420 may capture one or more still or moving images. The portable device 1430 may also connect to or otherwise communicate with the network 1402 through the sending and receiving of digital data.

The portable device 1430 may be used in any location and any environment to generate 2D body images that represent a body of the user. In some implementations, the portable device may be positioned such that it is stationary and approximately vertical (within approximately ten-degrees of vertical) and the user may position their body within a field of view of the imaging element 1420 of the portable device at different directions so that the imaging element 1420 of the portable device may generate 2D body images that include a representation of the body of the user from different directions, also referred to herein as 2D body direction images.

The portable device 1430 may also include one or more applications 1425, such as presentation application 1425-1, stored in memory that may be executed by the one or more processors 1426 of the portable device to cause the processor of the portable device to perform various functions or actions. For example, when executed, the application 1425 may provide instructions to a user regarding placement of the portable device, positioning of the body of the user within the field of view of the imaging element 1420 of the portable device, pose of the body, direction of the body, etc. Likewise, in some implementations, the presentation application 1425-1 may present a 3D body model and/or determined body fat measurement values, generated from the 2D body images in accordance with the described implementations, to the user and allow the user to interact with the 3D body model and/or body fat measurement values. For example, a user may rotate the 3D body model to view different angles of the 3D body model, obtain approximately accurate measurements of the body of the user from the dimensions of the 3D body model, view body measurements, such as body fat, body mass, volume, etc.

The application may also include or communicate with one or more neural networks, such as a body point location neural network 1450-1, pose determination neural network 1450-2, a 2D body direction image selection neural network 1450-3, and/or a body fat measurement determination neural network 1450-4, that are maintained in the memory 1424 of the portable device 1430 and executed by the one or more processors 1426 of the portable device 1430. As discussed above, the body point location neural network may receive one or more 2D body images from the imaging element 1420, process those images and generate, for each received image, a heat map indicating predicted body point locations. The pose determination neural network 1450-2 may receive as inputs the heat map produced by the body point location neural network 1450-1 and further process that heat map to determine whether the body represented in the 2D body image is in a defined pose, such as an A Pose. The 2D body direction image selection neural network 1450-3 may also receive the heat map and/or the 2D body images and further process that information to determine body direction confidence scores for a plurality of 2D body images and to select a 2D body image as the 2D body direction image for a determined body direction. The body fat measurement determination neural network 1450-4 may receive one or more 2D body images and/or one or more normalized body images and process those images to determine a body fat measurement value representation illustrative of the body fat of the body represented in the image(s).

Machine learning tools, such as artificial neural networks, have been utilized to identify relations between respective elements of apparently unrelated sets of data. An artificial neural network, such as CNN, is a parallel distributed computing processor comprised of individual units that may collectively learn and store experimental knowledge, and make such knowledge available for use in one or more applications. Such a network may simulate the non-linear mental performance of the many neurons of the human brain in multiple layers by acquiring knowledge from an environment through one or more flexible learning processes, determining the strengths of the respective connections between such neurons, and utilizing such strengths when storing acquired knowledge. Like the human brain, an artificial neural network may use any number of neurons in any number of layers, including an input layer, an output layer, and one or more intervening hidden layers. In view of their versatility, and their inherent mimicking of the human brain, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses have been utilized in image processing applications.

Artificial neural networks may be trained to map inputted data to desired outputs by adjusting the strengths of the connections between one or more neurons, which are sometimes called synaptic weights. An artificial neural network may have any number of layers, including an input layer, an output layer, and any number of intervening hidden layers. Each of the neurons in a layer within a neural network may receive one or more inputs and generate one or more outputs in accordance with an activation or energy function, with parameters corresponding to the various strengths or synaptic weights. Likewise, each of the neurons within a network may be understood to have different activation or energy functions; in this regard, such a network may be dubbed a heterogeneous neural network. In some neural networks, at least one of the activation or energy functions may take the form of a sigmoid function, wherein an output thereof may have a range of zero to one or 0 to 1. In other neural networks, at least one of the activation or energy functions may take the form of a hyperbolic tangent function, wherein an output thereof may have a range of negative one to positive one, or −1 to +1. Thus, the training of a neural network according to an identity function results in the redefinition or adjustment of the strengths or weights of such connections between neurons in the various layers of the neural network, in order to provide an output that most closely approximates or associates with the input to the maximum practicable extent.

Artificial neural networks may typically be characterized as either feedforward neural networks or recurrent neural networks, and may be fully or partially connected. In a feedforward neural network, e.g., a CNN, information specifically flows in one direction from an input layer to an output layer, while in a recurrent neural network, at least one feedback loop returns information regarding the difference between the actual output and the targeted output for training purposes. Additionally, in a fully connected neural network architecture, each of the neurons in one of the layers is connected to all of the neurons in a subsequent layer. By contrast, in a sparsely connected neural network architecture, the number of activations of each of the neurons is limited, such as by a sparsity parameter.

Moreover, the training of a neural network is typically characterized as supervised or unsupervised. In supervised learning, a training set comprises at least one input and at least one target output for the input. Thus, the neural network is trained to identify the target output, to within an acceptable level of error. In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize the error in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

Once a neural network has been trained to recognize dominant characteristics of an input of a training set, e.g., to associate an image with a label, a category, a cluster or a pseudolabel thereof, to within an acceptable tolerance, an input and/or multiple inputs, in the form of an image, features, known traits corresponding to the image, etc., may be provided to the trained network, and an output generated therefrom. For example, one of the neural network discussed above may receive as inputs a 2D body direction image. The trained neural network may then produce as outputs the probability that the body is a particular body direction. As another example, one of the neural network discussed above may receive as inputs the 2D body direction image and generate as outputs a heat map indicating for each x, y coordinate of the heat map a probability that the coordinate corresponds to a body point of the body represented in the 2D body direction image.

Returning to FIG. 14, the application 1425, upon selection of a 2D body direction image by the 2D body direction image selection neural network 1450-3 may send, via the network 1402, the selected 2D body direction image to the computing resources 1403 for processing by the 3D body model system 1401.

Generally, the 3D body model system 1401 includes computing resource(s) 1403. The computing resource(s) 1403 are separate from the portable device 1430. Likewise, the computing resource(s) 1403 may be configured to communicate over the network 1402 with the portable device 1430 and/or other external computing resources, data stores, etc.

As illustrated, the computing resource(s) 1403 may be remote from the portable device 1430 and implemented as one or more servers 1403(1), 1403(2), . . . , 1403(P) and may, in some instances, form a portion of a network-accessible computing platform implemented as a computing infrastructure of processors, storage, software, data access, and so forth that is maintained and accessible by components/devices of the 3D body model system 1401 and/or the portable device 1430 via the network 1402, such as an intranet (e.g., local area network), the Internet, etc. The computing resources 1403, which may include one or more neural network, may process one or more 2D body direction images representative of a body of a user, generate therefrom 3D body model parameters and/or body measurements, and send those 3D body model parameters and/or body measurements to the portable device 1430.

The computing resource(s) 1403 do not require end-user knowledge of the physical location and configuration of the system that delivers the services. Common expressions associated for these remote computing resource(s) 1403 include "on-demand computing," "software as a service (SaaS)," "platform computing," "network-accessible platform," "cloud services," "data centers," and so forth. Each of the servers 1403(1)-(P) include a processor 1417 and memory 1419, which may store or otherwise have access to an 3D body model system 1401.

The network 1402 may be any wired network, wireless network, or combination thereof, and may comprise the Internet in whole or in part. In addition, the network 1402 may be a personal area network, local area network, wide area network, cable network, satellite network, cellular telephone network, or combination thereof. The network 1402 may also be a publicly accessible network of linked networks, possibly operated by various distinct parties, such as the Internet. In some implementations, the network 1402 may be a private or semi-private network, such as a corporate or university intranet. The network 1402 may include one or more wireless networks, such as a Global System for Mobile Communications (GSM) network, a Code Division Multiple Access (CDMA) network, a Long Term Evolution (LTE) network, or some other type of wireless network. Protocols and components for communicating via the Internet or any of the other aforementioned types of communication networks are well known to those skilled in the art of computer communications and thus, need not be described in more detail herein.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, 3D body model, body measurements, and/or any other aspect of the present disclosure.

The 3D body model system 1401, the application 1425, and/or the portable device 1430 may use any web-enabled or Internet applications or features, or any other client-server applications or features including E-mail or other messaging techniques, to connect to the network 1402, or to communicate with one another, such as through short or multimedia messaging service (SMS or MMS) text messages. For example, the servers 1403-1, 1403-2 . . . 1403-P may be adapted to transmit information or data in the form of synchronous or asynchronous messages from the 3D body model system 1401 to the processor 1426 or other components of the portable device 1430, or any other computer device in real time or in near-real time, or in one or more offline processes, via the network 1402. Those of ordinary skill in the pertinent art would recognize that the 3D body model system 1401 may operate any of a number of computing devices that are capable of communicating over the network, including but not limited to set-top boxes, personal digital assistants, digital media players, web pads, laptop computers, desktop computers, electronic book readers, cellular phones, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the servers 1403-1, 1403-2 . . . 1403-P, the processor 1426, or any other computers or control systems utilized by the application 1425, the 3D body model system 1401, and/or the portable device 1430, and having sequences of instructions which, when executed by a processor (e.g., a central processing unit, or "CPU"), cause the processor to perform all or a portion of the functions, services and/or methods described herein. Such computer executable instructions, programs, software and the like may be loaded into the memory of one or more computers using a drive mechanism associated with the computer readable medium, such as a floppy drive, CD-ROM drive, DVD-ROM drive, network interface, or the like, or via external connections.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

Additionally, in accordance with the present disclosure, the training of machine learning tools (e.g., artificial neural networks or other classifiers) and the use of the trained machine learning tools to detect body pose, determine body point locations, determined body direction, to generate 3D body models of a body based on one or more 2D body images, and/or to determine body fat measurement values of a body from one or more 2D body images may occur on multiple, distributed computing devices, or on a single computing device, as described herein.

Still further, while the above implementations are described with respect generating 3D body models and body fat measurement values of human bodies represented in 2D body images, in other implementations, non-human bodies, such as dogs, cats, or other animals may be modeled in 3D and/or body fat measurements determined based on 2D images of those bodies. Accordingly, the use of a human body in the disclosed implementations should not be considered limiting.

It should be understood that, unless otherwise explicitly or implicitly indicated herein, any of the features, characteristics, alternatives or modifications described regarding a particular implementation herein may also be applied, used, or incorporated with any other implementation described herein, and that the drawings and detailed description of the present disclosure are intended to cover all modifications, equivalents and alternatives to the various implementations as defined by the appended claims. Moreover, with respect to the one or more methods or processes of the present disclosure described herein, including but not limited to the flow charts shown in FIGS. 4 through 6, 9, 11, and 13 or the transition diagrams shown in FIG. 1, orders in which such methods or processes are presented are not intended to be construed as any limitation on the claimed inventions, and any number of the method or process steps or boxes described herein can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain implementations could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

The elements of a method, process, or algorithm described in connection with the implementations disclosed herein can be embodied directly in hardware, in a software module stored in one or more memory devices and executed by one or more processors, or in a combination of the two. A software module can reside in RAM, flash memory, ROM, EPROM, EEPROM, registers, a hard disk, a removable disk, a CD-ROM, a DVD-ROM or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain implementations require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
   receiving, from a portable device, a two-dimensional ("2D") body image generated by a 2D camera of the portable device;
   processing the 2D body image at a first bottleneck of a neural network to produce a first downsampled feature representation;
   processing the first downsampled feature representation with a second bottleneck of the neural network to produce a second downsampled feature representation;
   extracting first features from the second downsampled feature representation;
   processing the second downsampled feature representation with a third bottleneck of the neural network to produce a third downsampled feature representation;
   extracting second features from the third downsampled feature representation;
   concatenating at least the first features, the second features, and an output of the neural network to produce concatenated features;
   applying a linear function to the concatenated features to determine a body fat measurement representation;
   determining a body fat measurement value from the body fat measurement representation; and
   presenting, via a display of the portable device, the body fat measurement value.

2. The computer-implemented method of claim 1, further comprising:
   processing the third downsampled feature representation with a fourth bottleneck of the neural network to produce a fourth downsampled feature representation;
   extracting third features from the fourth downsampled feature representation;
   processing the fourth downsampled feature representation with a fifth bottleneck of the neural network to produce a fifth downsampled feature representation;
   extracting fourth features from the fifth downsampled feature representation; and
   wherein concatenating includes concatenating the first features, the second features, the third features, the fourth features, and the output of the neural network to produce the concatenated features.

3. The computer-implemented method of claim 2, further comprising:
   applying a second linear function to the fifth downsampled feature representation to produce the output of the neural network.

4. The computer-implemented method of claim 1, further comprising:

segmenting the 2D body image to determine a first plurality of pixels that represent a body represented in the 2D body image;

suppressing a second plurality of pixels corresponding to a background of the 2D body image to produce a background suppressed image;

normalizing the background suppressed image to produce a normalized body image, wherein normalizing the background suppressed image includes adjusting a first size of the body to a first defined size and adjusting a second size of the background suppressed image to a second defined size; and wherein processing the 2D body image includes processing the normalized body image.

5. A computing system, comprising:

one or more processors; and a memory storing program instructions that, when executed by the one or more processors cause the one or more processors to at least:

receive a two-dimensional ("2D") body image of a body;

produce, from the 2D body image, a normalized body image having a defined size;

process the normalized body image with a neural network to determine a body fat measurement representation of the body;

determine a loss function indicating a discrepancy between the body fat measurement representation and an anchor body fat measurement representation; and provide the loss function to the neural network to update the neural network.

6. The computing system of claim 5, wherein the program instructions that, when executed by the one or more processors, further cause the one or more processors to at least:

determine, based at least in part on the body fat measurement representation, a body fat measurement value; and provide, for presentation, the body fat measurement value.

7. The computing system of claim 5, wherein the program instructions that, when executed by the one or more processors to process the normalized body image with the neural network, further include instructions that, when executed by the one or more processors further cause the one or more processors to at least:

process the normalized body image through a plurality of bottlenecks of the neural network, wherein each bottleneck produces a downsampled feature representation corresponding to the normalized body image;

extract, from each downsampled feature representation, corresponding features;

concatenate each of the extracted features and an output from the neural network to produce concatenated features; and process the concatenated features to determine the body fat measurement representation.

8. The computing system of claim 5, wherein:

the program instructions that, when executed by the one or more processors, further cause the one or more processors to at least:

produce, from a second 2D body image of the body, a second normalized body image; and the program instructions, that when executed by the one or more processors to process the normalized body image with the neural network, further include instructions that, when executed by the one or more processors, further cause the one or more processors to at least:

process the normalized body image and the second normalized body image with at least the neural network to determine the body fat measurement representation.

9. The computing system of claim 5, wherein the program instructions that, when executed by the one or more processors cause the one or more processors to produce, from the 2D body image, a normalized body image, further include instructions that, when executed by the one or more processors further cause the one or more processors to at least:

segment the 2D body image to determine a first plurality of pixels corresponding to the body and a second plurality of pixels that do not correspond to the body;

suppress the second plurality of pixels to produce a suppressed body image in which the first plurality of pixels are not suppressed, and the second plurality of pixels are suppressed; and normalize the suppressed body image to produce the normalized body image, wherein normalization of the suppressed body image includes adjusting a size of the suppressed body image to the defined size.

10. The computing system of claim 5, wherein the program instructions that, when executed by the one or more processors cause the one or more processors to determine the loss function, further include instructions that, when executed by the one or more processors further cause the one or more processors to at least:

determine a distribution of an anchor body fat measurement representation, wherein the anchor body fat measurement representation is based at least in part on body fat measurements obtained from a third party;

determine a divergence between the distribution of the anchor body fat measurement representation and the body fat measurement representation; and wherein the loss function includes the divergence.

11. The computing system of claim 5, wherein:

the program instructions that, when executed by the one or more processors further cause the one or more processors to at least:

determine, based at least in part on the body fat measurement representation, a body fat measurement value of the body; and wherein the program instructions that, when executed by the one or more processors cause the one or more processors to determine the loss function, further include instructions that, when executed by the one or more processors further cause the one or more processors to at least:

determine an anchor body fat measurement value, wherein the anchor body fat measurement value is based at least in part on body fat measurements obtained from a third party;

determine an absolute difference between the anchor body fat measurement value and the body fat measurement value; and wherein the loss function includes the absolute difference.

12. The computing system of claim 11, wherein the third party is at least one of: a plurality of human annotators, a third party body fat measurement system, or body images that include metadata with previously determined body fat measurement values.

13. The computing system of claim 5, wherein:

the 2D body image is generated from a 2D camera of a portable device; and the one or more processors and the memory are included in the portable device.

14. The computing system of claim 5, wherein:
the 2D body image is generated from a 2D camera of a portable device; and
the one or more processors and the memory are included in a computing system that is separate from the portable device.

15. A method comprising:
processing a two-dimensional ("2D") body image of a body to produce a first downsampled feature representation of the body;
extracting first features from the first downsampled feature representation;
processing the first downsampled feature representation of the body to produce a second downsampled feature representation of the body;
extracting second features from the second downsampled feature representation;
concatenating the first features and the second features to produce concatenated features of the body;
determining, based at least in part on the concatenated features of the body, a body fat measurement representation corresponding to the body; and
determining, based at least in part on the body fat measurement representation, a body fat measurement value representative of a body fat of the body.

16. The method of claim 15, wherein the 2D body image includes a representation of less than all of the body.

17. The method of claim 15, wherein:
the first downsampled feature representation includes spatial dimensions and a plurality of channels; and
extracting the first features from the first downsampled feature representation includes averaging the plurality of channels across the spatial dimension.

18. The method of claim 15, wherein:
processing the 2D body image further includes:
processing the 2D body image with a first bottleneck of a neural network to produce the first downsampled feature representation; and
processing the first downsampled feature representation further includes:
processing the first downsampled feature representation with a second bottleneck of the neural network to produce the second downsampled feature representation.

19. The method of claim 18, further comprising:
generating output features of the neural network from the second bottleneck of the neural network; and
wherein concatenating includes concatenating the first features, the second features, and the output features to produce concatenated features.

20. The method of claim 18, wherein:
a second spatial resolution of the second downsampled feature representation is lower than a first spatial resolution of the first downsampled feature representation.

21. A computer-implemented method, comprising:
determining, based at least in part on a concatenation of first features determined from a first two-dimensional body image of a body and second features extracted from a feature representation of the body, a body fat measurement value representative of a body fat of the body:,
determining, based at least in part on the body fat measurement value, a loss function; and
providing the loss function to a neural network to update the neural network.

22. The computer-implemented method of claim 21, further comprising:
determining a body fat measurement representation; and
wherein determining the body fat measurement value is based at least in part on the body fat measurement representation.

* * * * *